US012765790B2

(12) United States Patent
Wang et al.

(10) Patent No.: US 12,765,790 B2
(45) Date of Patent: Oct. 20, 2026

(54) BLOOD PRESSURE AND HEART RATE MEASURING DEVICE

(71) Applicant: Micro-Nano Development Co., Ltd., Taipei City (TW)

(72) Inventors: Yu-Jie Wang, New Taipei City (TW); Chi-Hung Tseng, New Taipei City (TW); Jiung-Ming Torng, New Taipei City (TW); Li-Karn Wang, Taipei City (TW)

(73) Assignee: MICRO-NANO DEVELOPMENT CO., LTD., Taipei City (TW)

( * ) Notice: Subject to any disclaimer, the term of this patent is extended or adjusted under 35 U.S.C. 154(b) by 239 days.

(21) Appl. No.: 18/751,525

(22) Filed: Jun. 24, 2024

(65) Prior Publication Data

US 2025/0339044 A1 Nov. 6, 2025

(30) Foreign Application Priority Data

May 3, 2024 (TW) ................................ 113116530

(51) Int. Cl.
*A61B 5/024* (2006.01)
*A61B 5/021* (2006.01)

(52) U.S. Cl.
CPC ...... *A61B 5/02416* (2013.01); *A61B 5/02108* (2013.01); *A61B 5/02405* (2013.01)

(58) Field of Classification Search
CPC ............ A61B 5/02416; A61B 5/02405; A61B 5/02108
See application file for complete search history.

(56) References Cited

U.S. PATENT DOCUMENTS

| | | | |
|---|---|---|---|
| 11,000,265 | B1 | 5/2021 | Ryu et al. |

FOREIGN PATENT DOCUMENTS

| | | | |
|---|---|---|---|
| CN | 100551284 | C | 10/2009 |
| CN | 204318732 | U | 5/2015 |
| CN | 104027108 | B | 6/2016 |
| CN | 104382568 | B | 8/2016 |
| CN | 106510620 | A | 3/2017 |
| CN | 107233097 | A | 10/2017 |
| CN | 107405114 | A | 11/2017 |
| CN | 115003218 | A | 9/2022 |

(Continued)

OTHER PUBLICATIONS

Tseng, "Low-Cost Blood Pressure Estimation Using Dual Fiber Bragg Gratings for Pulse Waveform Measurement", Jul. 26, 2023, Total 50 pages.

(Continued)

*Primary Examiner* — Eric F Winakur
*Assistant Examiner* — Sienna C Pyle
(74) *Attorney, Agent, or Firm* — Birch, Stewart, Kolasch & Birch, LLP

(57) ABSTRACT

A blood pressure and heart rate measuring device has two fiber gratings for converting broadband light into a narrowband ray. The reflection wavelength band and the transmission wavelength band of one of the two fiber gratings will shift with the vascular pulsating stress of an object to be measured, which will change the optical power of the narrowband ray. Therefore, the pulse waveform obtained by the blood pressure and heart rate measuring device based on the optical power of the narrowband ray can be used to determine a blood pressure and a heart rate.

17 Claims, 17 Drawing Sheets

(56) References Cited

FOREIGN PATENT DOCUMENTS

| | | | | |
|---|---|---|---|---|
| JP | 2004170313 | A | * | 6/2004 |
| JP | 2015-231512 | A | | 12/2015 |
| WO | WO 2021/127207 | A1 | | 6/2021 |

OTHER PUBLICATIONS

Wang, "Blood Pressure Measurement Using Fiber Bragg Grating Sensor with Optical Power Detection Scheme", Jul. 26, 2023, Total 83 pages.

* cited by examiner

BLOOD PRESSURE AND HEART RATE MEASURING DEVICE

BACKGROUND OF THE INVENTION

This application claims priority for the TW application No. 113116530 filed on 3 May 2024, the content of which is incorporated by reference in its entirety.

FIELD OF THE INVENTION

The present invention relates to a device and a method for non-invasively measuring a blood pressure and a heart rate using fiber gratings, particularly to a device and a method for measuring the waveform of vascular pulsation based on optical power to calculate a blood pressure and a heart rate.

DESCRIPTION OF THE RELATED ART

The present methods for measuring a blood pressure and a heart rate are divided into two types, namely an invasive type and a non-invasive type. The invasive method, usually used to measure the blood pressures and the heart rates of patients in intensive care units and operating rooms, involves inserting a needle into the arteries of the subject (such as a patient). However, invasive methods have the risk of infection. Non-invasive blood pressure and heart rate measurement, used by the general public, has relatively convenient and non-invasive advantages. Currently, the most commonly used method for non-invasive blood pressure and heart rate measurement involves the use of an inflatable cuff. The cuff is inflated and then gradually deflated to allow blood to flow through the brachial or radial arteries, thereby generating oscillating pulse wave signals. These signals are detected by a pulsation sensor within the cuff to obtain the values of systolic and diastolic blood pressures. However, since this method requires inflating the cuff prior to measurement, it is not suitable for continuously monitoring a blood pressure and a heart rate.

To overcome the foregoing drawbacks, researchers between 2013 and 2019 proposed using fiber Bragg grating (FBG) sensors for blood pressure and heart rate measurement. Examples include U. Sharath, R. Sukreet, G. Apoorva, and S. Asokan's work, "Blood pressure evaluation using sphygmomanometry assisted by arterial pulse waveform detection by fiber Bragg grating pulse device," published in the Journal of Biomedical Optics, 18 (6): 067010, 2013; D. Jia, J. Chao, S. Li, H. Zhang, Y. Yan, T. Liu, and Y. Sun's paper, "A fiber Bragg grating sensor for radial artery pulse waveform measurement," published in IEEE Transactions on Biomedical Engineering, vol. 65, no. 4, pp. 839-846, 2018; and Hiroaki Ishizawa et al.'s study, "Measurement of pulse wave signals and blood pressure by a plastic optical fiber FBG sensor," published in Sensors, 19 (23): 5088, 2019. These studies measure vascular pulse waveforms (hereinafter referred to as pulse waveforms) by detecting changes in the reflection wavelength of the fiber Bragg grating in order to obtain the values of blood pressures and heart rates.

Additionally, in 2019, U.S. Pat. No. 10,376,160 B2 provided an optical method combined with a blood pressure calibration model for measuring blood pressure. In this patent, a single fiber grating is used to sense vascular pulsation signals, and a Mach-Zehnder interferometer is employed to obtain the pulsation signals as pulse waveforms. These waveforms are then processed by a blood pressure value calculation unit to determine blood pressure values. In 2022, U.S. Pat. No. 11,504,010 B2 provided a wearable device where two sets of fiber gratings are placed on the wrist. This device detects changes in wavelength and estimates blood pressure values in cooperation with a blood pressure estimation model.

However, the current pulse waveforms are generated due to the time-domain variation of the reflection wavelength (commonly known as the Bragg wavelength) of the fiber grating. A wavelength detection instrument is often used to capture the timing variation of the wavelength in order to obtain the pulse waveforms. This detection method is complex and expensive.

SUMMARY OF THE INVENTION

One of objectives of the present invention is to provide a blood pressure and heart rate measuring device and a method thereof using two fiber gratings, which obtain a pulse waveform by detecting optical power.

One of objectives of the present invention is to provide a protective structure for protecting fiber gratings and fiber optical paths.

One of objectives of the present invention is to provide a blood pressure and heart rate calculation method required by a blood pressure and heart rate measuring device.

According to the present invention, a blood pressure and heart rate measuring device includes at least a broadband light source, an optical coupler, a first fiber grating, a second fiber grating, and a first photo receiver. The broadband light source is configured to provide broadband light. The optical coupler is connected to the broadband light source through a first optical path and configured to receive the broadband light. The first fiber grating, connected to the optical coupler through a second optical path, has a first reflection wavelength band. The first fiber grating is configured to receive a first light ray from the optical coupler through the second optical path and reflect a part of the first light ray whose wavelength band is within the first reflection wavelength band to generate a second light ray that returns to the optical coupler along the second optical path. The first light ray is a part or all of the broadband light. The second fiber grating, connected to the optical coupler through a third optical path, has a second reflection wavelength band. The second fiber grating is configured to receive a third light ray from the optical coupler through the third optical path and allow a part of the third light ray whose wavelength band is not within the second reflection wavelength band to pass to generate a fourth light ray. The third light ray is a part or all of the second light ray. The first photo receiver is connected to the second fiber grating through a fourth optical path and configured to receive the fourth light ray from the second fiber grating through the fourth optical path and generate a first electrical signal of a pulse waveform of vascular pulsation in response to the fourth light ray. The first reflection wavelength band shifts with the vascular pulsating stress of an object to be measured.

According to the present invention, a blood pressure and heart rate measuring device includes at least a broadband light source, a first optical coupler, a first fiber grating, a second optical coupler, a second fiber grating, and a first photo receiver. The broadband light source is configured to provide broadband light. The first optical coupler is connected to the broadband light source through a first optical path and configured to receive the broadband light. The first optical coupler is configured to generate a first light ray and a second light ray in response to the broadband light and respectively transmit the first light ray and the second light ray to a second optical path and a third optical path. The first light ray and the second light ray are parts of the broadband light. The first fiber grating, connected to the first optical coupler through the second optical path and the third optical path, has a first reflection wavelength band. The first fiber grating is configured to reflect a part of the first light ray whose wavelength band is within the first reflection wavelength band to generate a third light ray that returns to the first optical coupler along the second optical path and to reflect a part of the second light ray whose wavelength band is within the first reflection wavelength band to generate a fourth light ray that returns to the first optical coupler along the third optical path. The second optical coupler is configured to receive a fifth light ray from the first optical coupler through a fourth optical path, generate a sixth light ray in response to the fifth light ray, and transmit the sixth light ray to a fifth optical path. The first optical coupler is configured to generate the fifth light ray in response to the third light ray and the fourth light ray, and the sixth light ray is a part or all of the fifth light ray. The second fiber grating, connected to the second optical coupler through a fifth optical path, has a second reflection wavelength band. The second fiber grating is configured to receive the sixth light ray from the second optical coupler through the fifth optical path and reflect a part of the sixth light ray whose wavelength band is within the second reflection wavelength band to generate a seventh light ray that returns to the second optical coupler along the fifth optical path. The first photo receiver is configured to receive an eighth light ray from the second optical coupler through a sixth optical path and generate a first electrical signal of the pulse waveform of vascular pulsation in response to the eighth light ray. The second reflection wavelength band shifts with the vascular pulsating stress of an object to be measured.

According to the present invention, a blood pressure and heart rate measuring device includes at least a laser light source, a first optical coupler, a first fiber grating, an Er-doped fiber, a second optical coupler, a second fiber grating, and a first photo receiver. The laser light source is configured to provide laser light. The first optical coupler is connected to the laser light source through a first optical path and configured to receive the laser light. The first optical coupler is configured to guide the laser light to a second optical path. The first fiber grating, connected to the first optical coupler through the second optical path, has a first reflection wavelength band and a first transmission wavelength band. The laser light from the first optical coupler passes through the first fiber grating. The Er-doped fiber is connected to the first fiber grating and configured to generate broadband light that returns to the first fiber grating in response to the laser light passing through the first fiber grating. A part of the broadband light whose wavelength band is within the first transmission wavelength band passes through the first fiber grating to generate a first light ray that returns to the first optical coupler along the second optical path. The second optical coupler is configured to receive a second light ray from the first optical coupler through a third optical path, generate a third light ray in response to the second light ray, and transmit the third light ray to a fourth optical path. The second light ray is a part or all of the first light ray and the third light ray is a part or all of the second light ray. The second fiber grating, connected to the second optical coupler through the fourth optical path, has a second reflection wavelength band and a second transmission wavelength band. The second fiber grating is configured to receive the third light ray from the second optical coupler through the fourth optical path and reflect a part of the third light ray whose wavelength band is within the second reflection wavelength band to generate a fourth light ray that returns to the second optical coupler along the fourth optical path. The first photo receiver is configured to receive a fifth light ray from the second optical coupler through a fifth optical path and generate a first electrical signal of the pulse waveform of vascular pulsation in response to the fifth light ray. The fifth light ray is a part or all of the fourth light ray. The second reflection wavelength band shifts with the vascular pulsating stress of an object to be measured.

According to the present invention, a blood pressure and heart rate measuring device includes at least a broadband light source, a first fiber grating, an optical coupler, a second fiber grating, and a first photo receiver. The broadband light source is configured to provide broadband light. The first fiber grating, connected to the broadband light source through a first optical path and configured to receive the broadband light, has a first reflection wavelength band and a first transmission wavelength band. A part of the broadband light whose wavelength band is within the first transmission wavelength band passes through the first fiber grating to form a first light ray. The optical coupler is connected to the first fiber grating through a second optical path and configured to receive the first light ray. The second fiber grating, connected to the optical coupler through a third optical path, has a second reflection wavelength band and a second transmission wavelength band. The second fiber grating is configured to receive a second light ray from the optical coupler through the third optical path and reflect a part of the second light ray whose wavelength band is within the second reflection wavelength band to generate a third light ray that returns to the optical coupler along the third optical path. The second light ray is a part or all of the first light ray. The first photo receiver is connected to the optical coupler through a fourth optical path and configured to receive a fourth light ray from the optical coupler through the fourth optical path and generate a first electrical signal of the pulse waveform of vascular pulsation in response to the fourth light ray. The fourth light ray is a part or all of the third light ray. The second reflection wavelength band shifts with the vascular pulsating stress of an object to be measured.

According to the present invention, a blood pressure and heart rate measuring device includes at least a broadband light source, an optical coupler, a first fiber grating, a second fiber grating, and a first photo receiver. The broadband light source is configured to provide broadband light. The optical coupler is connected to the broadband light source through a first optical path and configured to receive the broadband light. The first fiber grating, connected to the optical coupler through a second optical path, has a first reflection wavelength band and a first transmission wavelength band. The first fiber grating is configured to receive a first light ray from the optical coupler through the second optical path and reflect a part of the first light ray whose wavelength band is within the first reflection wavelength band to generate a second light ray that returns to the optical coupler along the second optical path. The first light ray is a part or all of the broadband light. A part of the first light ray whose wavelength band is within the first transmission wavelength band passes through the first fiber grating to form a third light ray. The second fiber grating, connected to the first fiber grating through a third optical path, has a second reflection wavelength band and a second transmission wavelength band. The second fiber grating is configured to receive the third light ray from the first fiber grating through the third optical path and reflect a part of the third light ray whose wavelength band is within the second reflection wavelength band to generate a fourth light ray that returns to the optical coupler along the third optical path, the first fiber grating, and the second optical path. The first photo receiver is connected to the optical coupler through a fourth optical path and configured to receive a fifth light ray from the optical coupler through the fourth optical path and generate a first electrical signal of the pulse waveform of vascular pulsation in response to the fifth light ray. The fifth light ray is parts or all of the second light ray and the fourth light ray. The first reflection wavelength band or the second reflection wavelength band shifts with the vascular pulsating stress of an object to be measured.

According to the present invention, a protective structure for protecting a fiber grating and a fiber optical path includes a stretchable material and a tube that is of plastic type or of rubber type. The stretchable material is configured to cover the fiber grating, a first fiber optical path, a second fiber optical path, and the first portion of a third fiber optical path. The third fiber optical path has a first portion inside the stretchable material, and a second portion outside the stretchable material. One end of the first fiber optical path is connected to the fiber grating and another end of the first fiber optical path is connected to the first portion of the third fiber optical path. The second fiber optical path has a second portion outside the stretchable material. The tube has a first portion and a second portion. The first portion of the tube, located inside the stretchable material, covers the first portion of the third fiber optical path. The second portion of the tube, located outside the stretchable material, covers the second portion of the third fiber optical path. A first light ray, entering the interior of the stretchable material from the third fiber optical path, is emitted to the fiber grating through the first fiber optical path. A part of the first light ray whose wavelength band is within the reflection wavelength band of the fiber grating is reflected to form a second light ray that returns to the first fiber optical path and then the third fiber optical path. The second light ray is received by a photo receiver to generate an electrical signal of the pulse waveform of vascular pulsation.

Below, the embodiments are described in detail in cooperation with the drawings to make easily understood the technical contents, characteristics and accomplishments of the present invention.

DETAILED DESCRIPTION OF THE INVENTION

Figure 1:
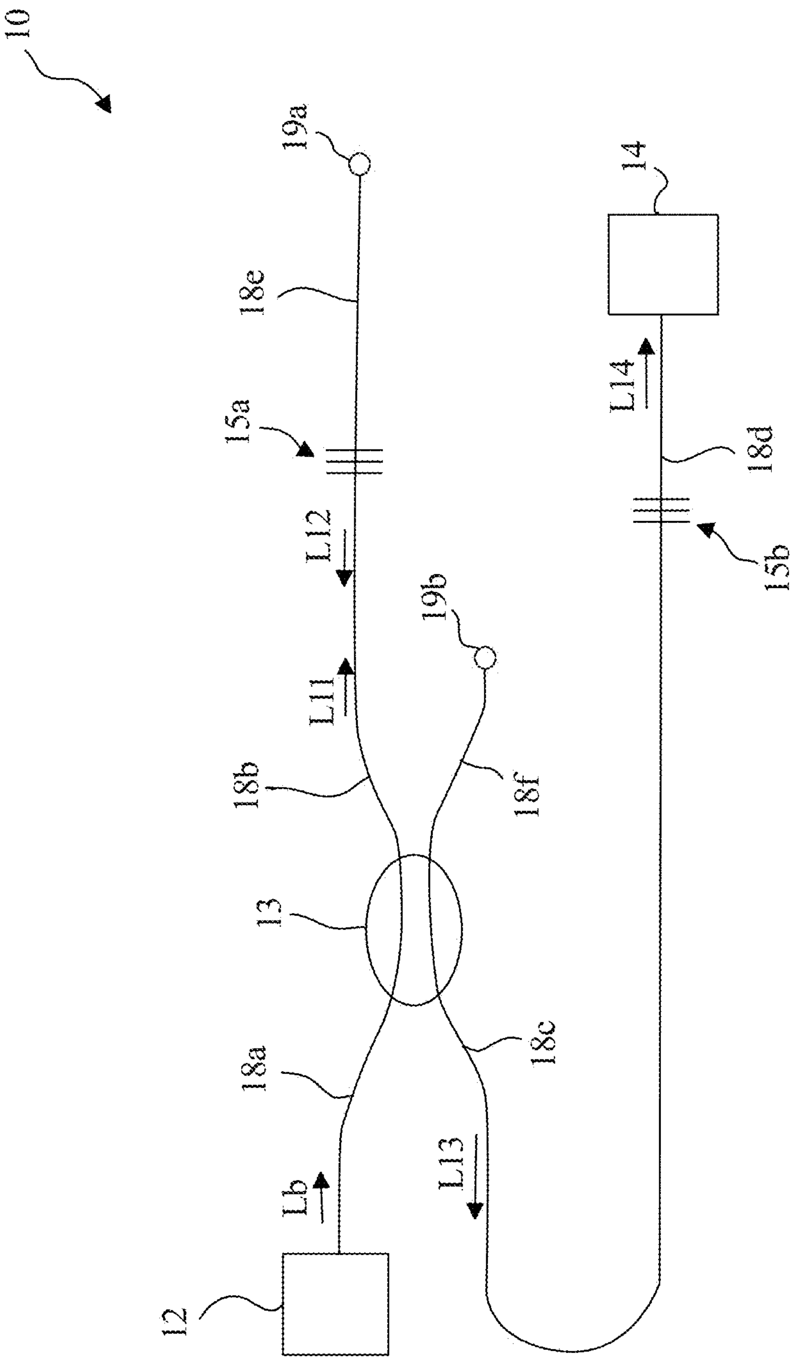
FIG. 1 is a schematic diagram showing a blood pressure and heart rate measuring device according to a first embodiment of the present invention.

FIG. 1 is a schematic diagram showing a blood pressure and heart rate measuring device according to a first embodiment of the present invention. As shown in FIG. 1, a blood pressure and heart rate measuring device 10 includes at least a broadband light source 12, an optical coupler 13, a first fiber grating 15*a*, a second fiber grating 15*b*, and a first photo receiver 14. The broadband light source 12 provides broadband light Lb for the optical coupler 13 through a first optical path 18*a*. The optical coupler 13 generates a first light ray L11 in response to the broadband light Lb and transmits the first light ray L11 to the first fiber grating 15*a* through a second optical path 18*b*. The first light ray L11 is a part or all of the broadband light Lb. The first fiber grating 15*a* has a first reflection wavelength band RB1 and a first transmission wavelength band TB1. The part of the first light beam L11 whose wavelength band is within the first reflection wavelength band RB1 will be reflected by the first fiber grating 15*a* to generate a second light ray L12 that returns to the optical coupler 13 along the second optical path 18*b*. After receiving the second light ray L12, the optical coupler 13 generates a third light ray L13 and guides it to the second fiber grating 15*b* along a third optical path 18*c*. The second fiber grating 15*b* has a second reflection wavelength band RB2 and a second transmission wavelength band TB2. The part of the third light ray L13 whose wavelength band is not within the second reflection wavelength band RB2 (i.e., within the second transmission wavelength band TB2) passes through the fiber grating 15*b* to form a fourth light ray L14. The first photo receiver 14 receives the fourth light ray L14 from the second fiber grating 15*b* through a fourth optical path 18*d* and generates a first electrical signal of the pulse waveform of vascular pulsation based on the optical power of the fourth light ray L14. The first electrical signal is converted into a current signal or voltage signal.

In FIG. 1, the first fiber grating 15*a* is adjacent to the surface of the object to be measured (such as human skin). Thus, the first fiber grating 15*a* will shift the first reflection wavelength band RB1 and the first transmission wavelength band TB1 due to vascular pulsating stress. The second fiber grating 15*b* is far away from the surface of the object to be measured. The second fiber grating 15*b* is less or not affected by the vascular pulsating stress. Therefore, the second reflection wavelength band RB2 and the second transmission wavelength band TB2 of the second fiber grating 15*b* will only shift slightly or not shift at all.

Figure 2:
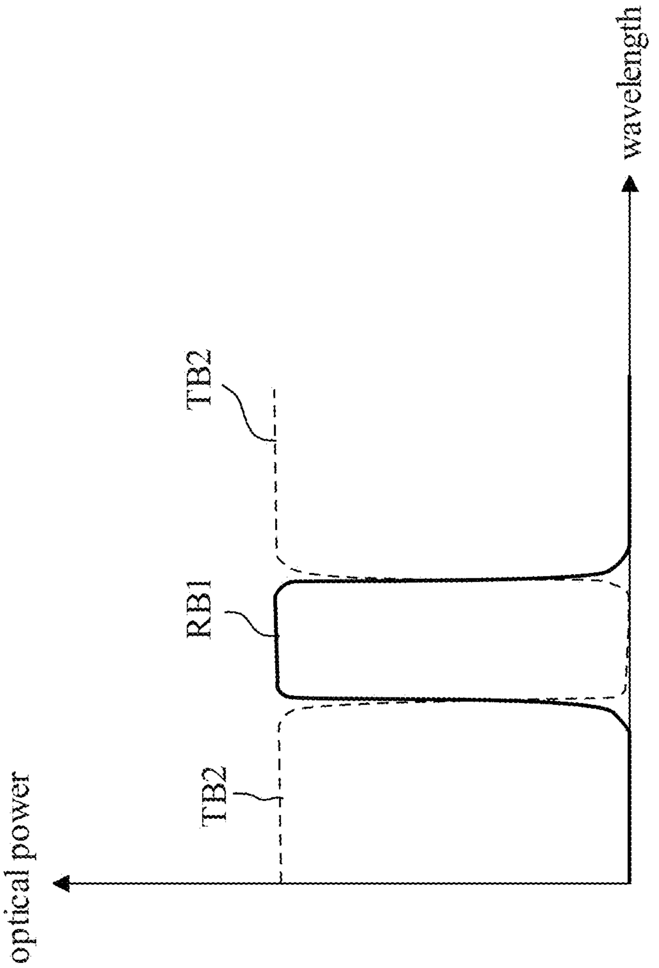
FIG. 2 is a schematic diagram showing the first reflection wavelength band RB1 of a first fiber grating 15*a* and the second transmission wavelength band TB2 of a second fiber grating 15*b* when not affected by vascular pulsating stress.

FIG. 2 is a schematic diagram showing the first reflection wavelength band RB1 of a first fiber grating 15*a* and the second transmission wavelength band TB2 of a second fiber grating 15*b* when not affected by vascular pulsating stress. When the first fiber grating 15*a* and the second fiber grating 15*b* have the same reflection wavelength band (that is, the first reflection wavelength band RB1 and the second reflection wavelength band RB2 are identical, such that the first reflection wavelength band RB1 and the second transmission wavelength band TB2 are complementary, as shown in FIG. 2). If the first fiber grating 15*a* does not bear any vascular pulsating stress, the wavelength band of the third light ray L13 is almost completely within the second reflection wavelength band RB2 of the second fiber grating 15*b*. In other words, the optical power of the fourth light ray L14 received by the first photo receiver 14 is very small or almost zero.

Figure 3:
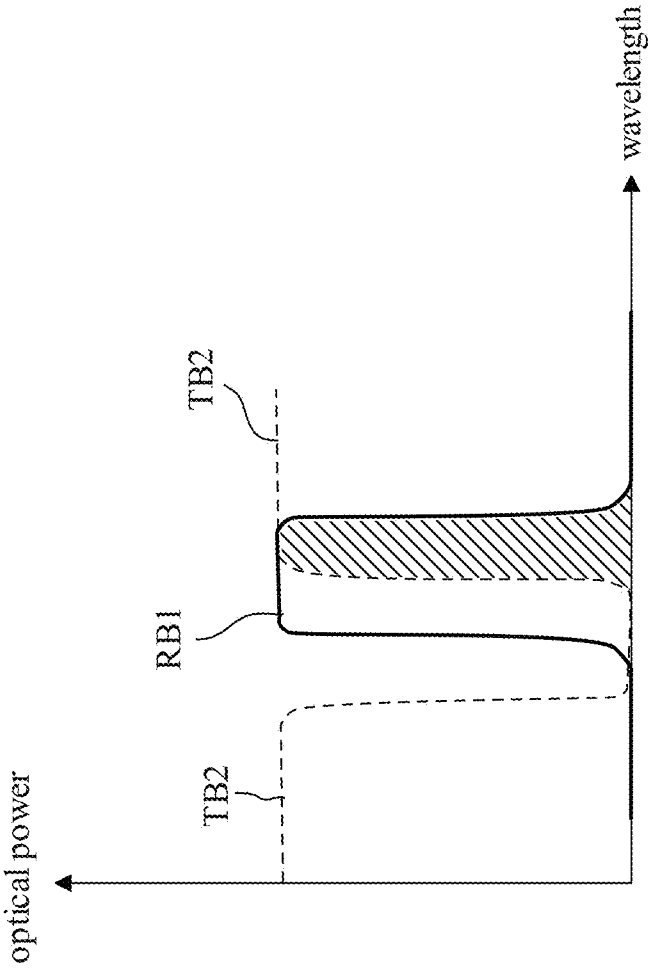
FIG. 3 is a schematic diagram showing the first reflection wavelength band RB1 of a first fiber grating 15*a* and the second transmission wavelength band TB2 of a second fiber grating 15*b* when affected by vascular pulsating stress.

FIG. 3 is a schematic diagram showing the first reflection wavelength band RB1 of a first fiber grating 15*a* and the second transmission wavelength band TB2 of a second fiber grating 15*b* when affected by vascular pulsating stress. When the first fiber grating 15*a* bears vascular pulsating stress such that the first reflection wavelength band RB1 shifts to the right, the first reflection wavelength band RB1 of the first fiber grating 15*a* will partially overlap the second transmission wavelength band TB2 of the second fiber grating 15*b*, as shown in the slash region of FIG. 3. The size of the slash region is directly proportional to the optical power of the fourth light ray L14 passing through the second fiber grating 15*b*. If the first fiber grating 15*a* bears lower vascular pulsating stress, the area of the slash region becomes smaller, the optical power of the fourth light ray L14 becomes lower, and thus the electrical signal outputted by the first photo receiver 14 becomes smaller. On the contrary, if the first fiber grating 15*a* bears higher vascular pulsating stress, the area of the slash region becomes larger, the optical power of the fourth light ray L14 becomes higher, and thus the electrical signal outputted by the first photo receiver 14 becomes larger. That is to say, when the vascular pulsating stress applied to the first fiber grating 15*a* fluctuates, the electrical signal outputted by the first photo receiver 14 fluctuates, thereby forming the pulse waveform of vascular pulsation.

In FIG. 1, the blood pressure and heart rate measuring device 10 further includes a fifth optical path 18*e* and a sixth optical path 18*f* respectively connected to the first fiber grating 15*a* and the optical coupler 13. In order to avoid Fresnel reflections at the end surfaces 19*a* and 19*b* of the fifth optical path 18*e* and the sixth optical path 18*f*, there are several ways to avoid reflecting light rays back into the optical paths: (1) coating anti-reflective materials on the end surfaces 19*a* and 19*b*; (2) designing the end faces 19*a* and 19*b* to have an inclination angle greater than 3 degrees; and (3) designing the optical paths near the end faces 19*a* and 19*b* to have curled shapes with small radiuses of curvature to produce the bending loss of light.

The first optical path 18*a*, the second optical path 18*b*, the third optical path 18*c*, the fourth optical path 18*d*, the fifth optical path 18*e*, and the sixth optical path 18*f* in FIG. 1 can be fiber optical paths, waveguide optical paths, or fiber and waveguide mixed optical paths.

Figure 4:
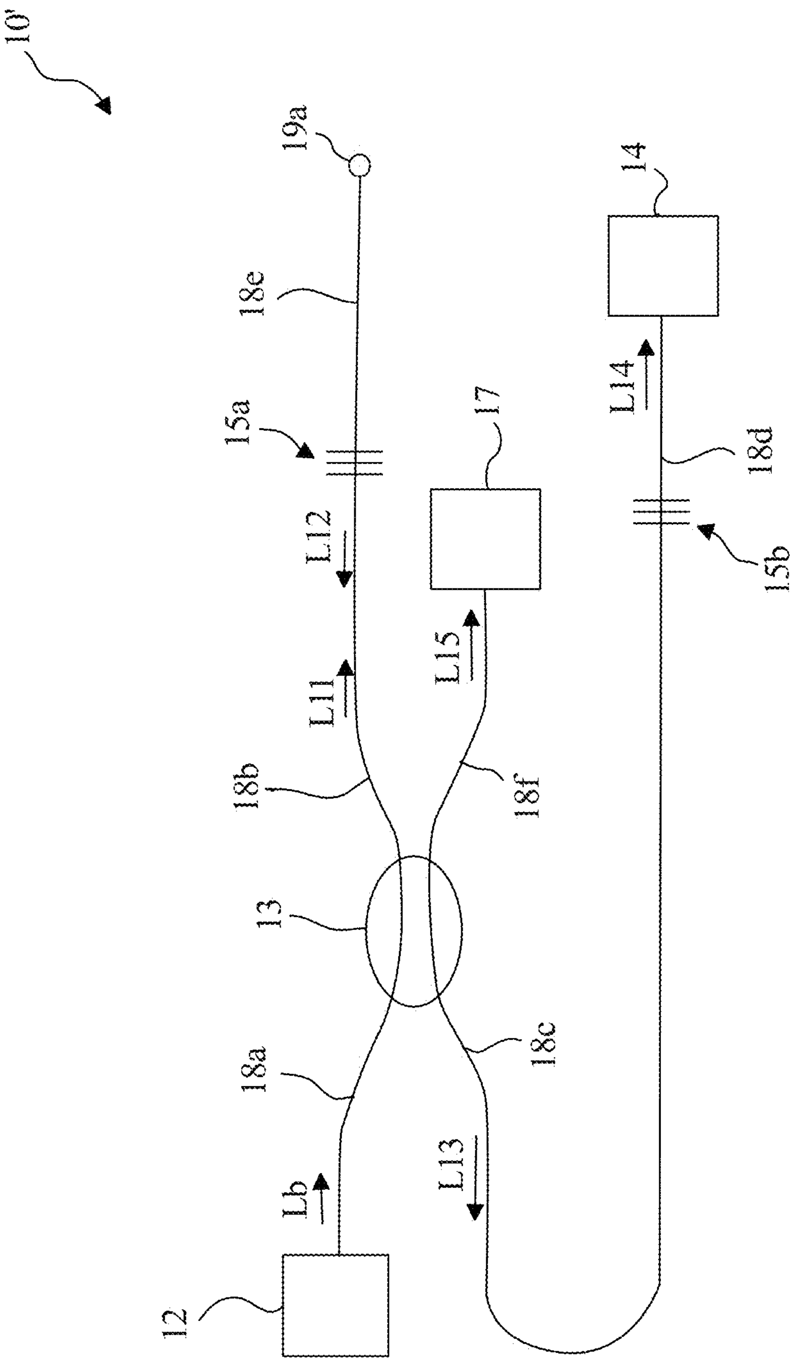
FIG. 4 is a schematic diagram showing a blood pressure and heart rate measuring device according to a second embodiment of the present invention.

FIG. 4 is a schematic diagram showing a blood pressure and heart rate measuring device according to a second embodiment of the present invention. The blood pressure and heart rate measuring device of FIG. 1 is almost the same as that of FIG. 4. Their difference is that the blood pressure and heart rate measuring device 10' of FIG. 4 further includes a second photo receiver 17 connected to the optical coupler 13 through a sixth optical path 18*f*. When the optical power of the broadband light source 12 is unstable, the optical power of the fourth light ray L14 received by the first photo receiver 14 will also be unstable, which may distort the finally obtained pulse waveform. The blood pressure and heart rate measuring device 10' employs the second photo receiver 17 to improve the problem. Specifically, after the optical coupler 13 receives the broadband light Lb, the optical coupler 13 will generate a fifth light ray L15 and transmit the fifth light ray L15 to the second photo receiver 17 through the sixth optical path 18*f*. The second photo receiver 17 generates a second electrical signal in response to the fifth light ray L15. Since the first electrical signal and the second electrical signal both include unstable components of the broadband light source 12, the blood pressure and heart rate measuring device 10' can cancel out the unstable components when dividing the first electrical signal by the second electrical signal. In other words, the pulsating waveform signal obtained by dividing the first electrical signal by the second electrical signal excludes the unstable component and will not be affected by the instability of the broadband light source 12.

Figure 5:
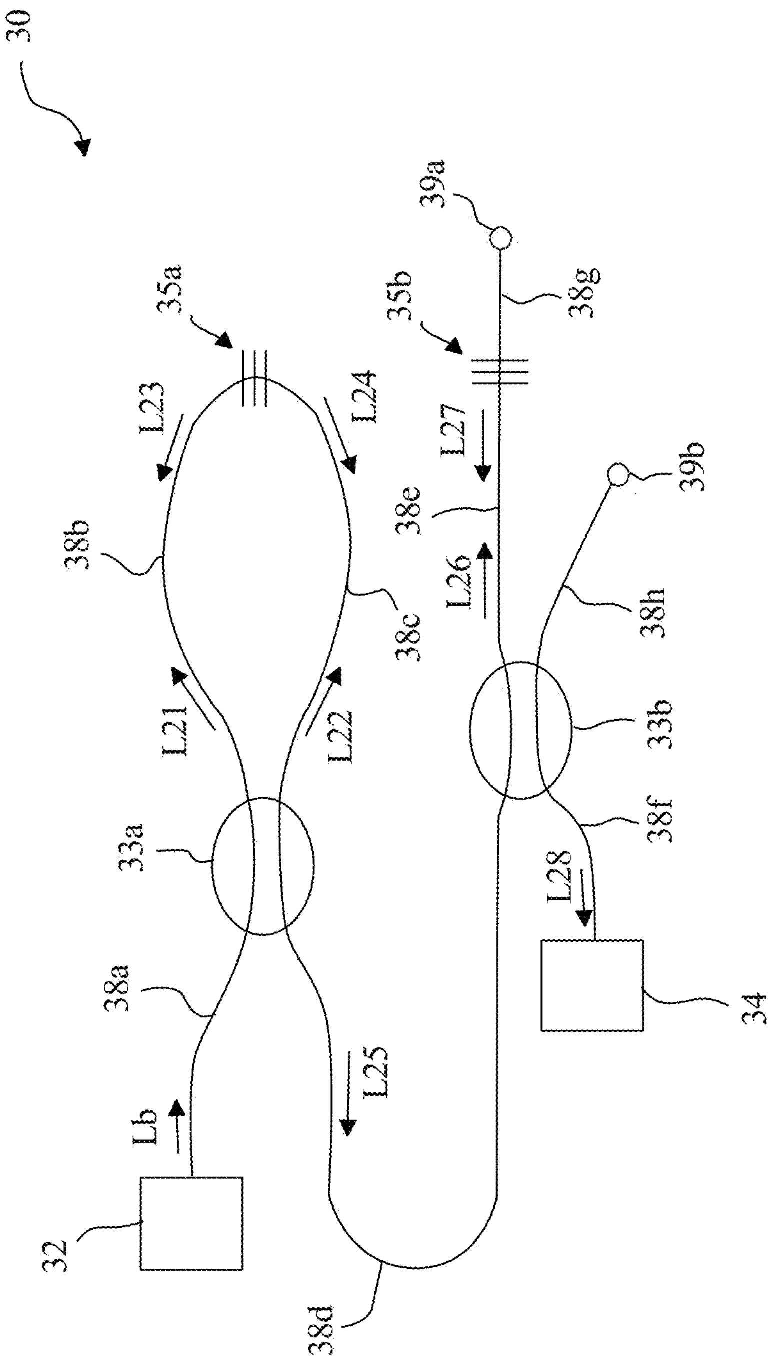
FIG. 5 is a schematic diagram showing a blood pressure and heart rate measuring device according to a third embodiment of the present invention.

FIG. 5 is a schematic diagram showing a blood pressure and heart rate measuring device according to a third embodiment of the present invention. The blood pressure and heart rate measuring device 30 of FIG. 5 includes at least a broadband light source 32, a first optical coupler 33*a*, a second optical coupler 33*b*, a first fiber grating 35*a*, a second fiber grating 35*b*, a first photo receiver 34. The broadband light source 32 provides broadband light Lb for the first photo coupler 33*a* through a first optical path 38*a*. The first optical coupler 33*a* generates a first light ray L21 and a second light ray L22 in response to the broadband light Lb and transmits the first light ray L21 and the second light ray L22 to the first fiber grating 35*a* through a second optical path 38*b* and a third optical path 38*c*, respectively. The first light ray L21 and the second light ray L22 is parts or all of the broadband light Lb. The first fiber grating 35*a* has a first reflection wavelength band RB1 and a first transmission wavelength band TB1. The part of the first light ray L21 whose wavelength band is within the first reflection wavelength band RB1 will be reflected by the first fiber grating 35*a* to generate a third light ray L23 that returns to the first optical coupler 33*a* along the second optical path 38*b*. The part of the second light ray L22 whose wavelength band is within the first reflection wavelength band RB1 will be reflected by the first fiber grating 35*a* to generate a fourth light ray L24 that returns to the first optical coupler 33*a* along the third optical path 38*c*. After receiving the third light ray L23 and the fourth light ray L24, the first optical coupler 33*a* generates a fifth light ray L25 and provides it for the second optical coupler 33*b* along a fourth optical path 38*d*, where the fifth light ray L25 is a part or all of the sum of the third light ray L23 and the fourth light ray L24. The second optical coupler 33*b* generates a sixth light ray L26 in response to the fifth light ray L25 and provides the sixth light ray L26 for the second fiber grating 35*b* through a fifth optical path 38*e*. The second fiber grating 35*b* has a second reflection wavelength band RB2 and a second transmission wavelength band TB2. The part of the sixth light ray L26 whose wavelength band is within the second reflection wavelength band RB2 is reflected by the second fiber grating 35*b* to generate a seventh light ray L27 that returns to the second optical coupler 33*b* along the fifth optical path 38*e*. The second optical coupler 33*b* generates an eighth light ray L28 in response to the seventh light ray L27 and provides the eighth light ray L28 for the first photo receiver 34 through a sixth optical path 38*f*. The first photo receiver 34 generates a first electrical signal of the pulse waveform of vascular pulsation based on the optical power of the eighth light ray L28, wherein the first electrical signal is converted into a current signal or a voltage signal. The eighth light ray L28 has a wavelength band within the overlapping wavelength band of the first reflection wavelength band RB1 and the second reflection wavelength band RB2.

In FIG. 5, the second fiber grating 35*b* is adjacent to the surface of an object to be measured (such as human skin). Thus, the second fiber grating 35*b* will shift the second reflection wavelength band RB2 and the second transmission wavelength band TB2 due to the vascular pulsating stress. Since the first fiber grating 35*a* is far away from the surface of the object to be measured, the first fiber grating 35*a* is less or not affected by the vascular pulsating stress. Therefore, the first reflection wavelength band RB1 and the first transmission wavelength band TB1 of the first fiber grating 35*a* will only shift slightly or not shift at all. When the second fiber grating 35*b* bears the vascular pulsating stress, the second reflection wavelength band RB2 shifts with vascular pulsation, which changes the area of the overlapping wavelength band of the first reflection wavelength band RB1 and the second reflection wavelength band RB2. In other words, the optical power of the eighth light ray L28 received by the first photo receiver 34 changes with the vascular pulsation. Thus, the optical power received by the first photo receiver 34 presents a pulse waveform signal.

In FIG. 5, the blood pressure and heart rate measuring device 30 further includes a seventh optical path 38*g* and an eighth optical path 38*h* respectively connected to the second fiber grating 35*b* and the second optical coupler 33*b*. In order to avoid Fresnel reflections at the end surfaces 39*a* and 39*b* of the seventh optical path 38*g* and the eighth optical path 38*h*, there are several ways to avoid reflecting light rays back into the optical paths: (1) coating anti-reflective materials on the end surfaces 39*a* and 39*b*; (2) designing the end faces 39*a* and 39*b* to have an inclination angle greater than 3 degrees; and (3) designing the optical paths near the end faces 39*a* and 39*b* to have curled shapes with small radiuses of curvature to produce the bending loss of light.

The first optical path 38*a*, the second optical path 38*b*, the third optical path 38*c*, the fourth optical path 38*d*, the fifth optical path 38*e*, the sixth optical path 38*f*, the seventh optical path 38*g*, and the eighth optical path 38*h* in FIG. 5 can be fiber optical paths, waveguide optical paths, or fiber and waveguide mixed optical paths.

Figure 6:
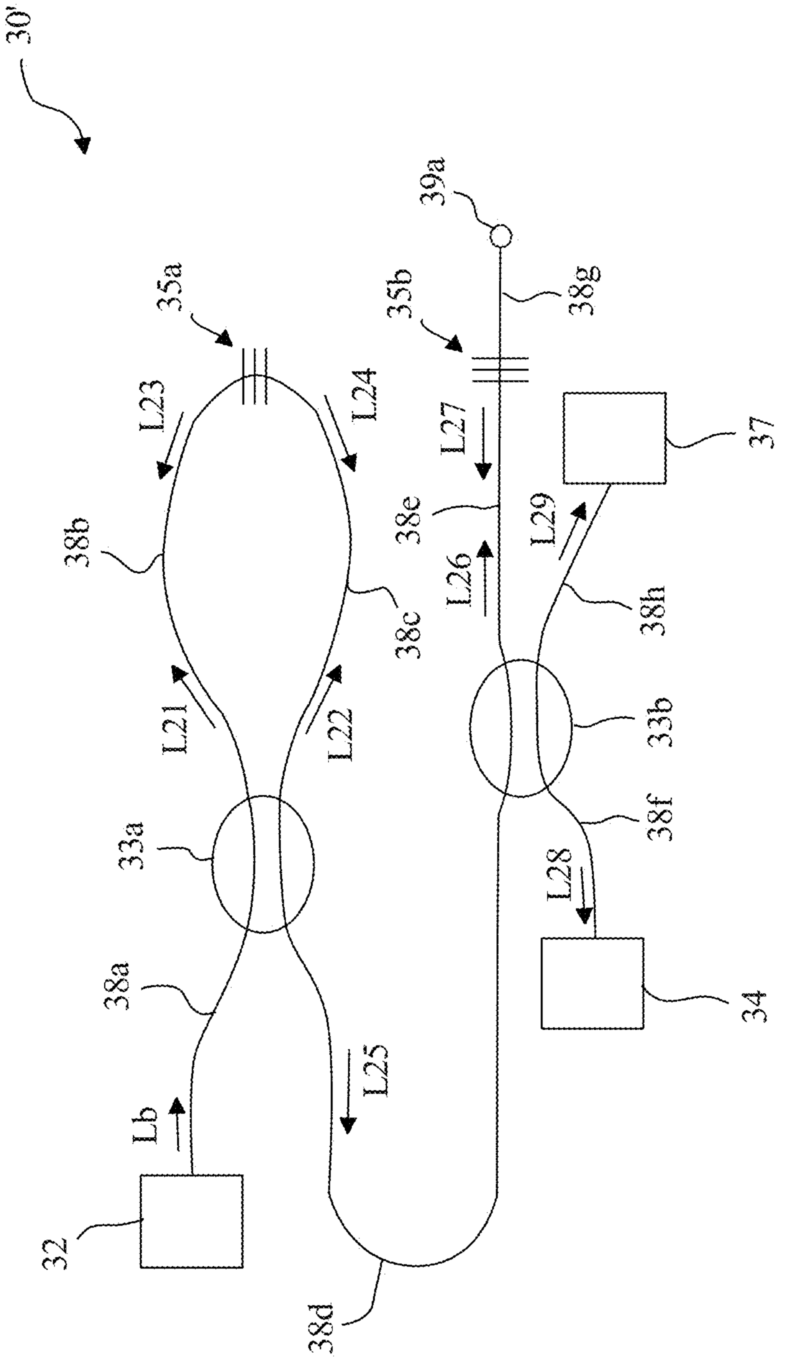
FIG. 6 is a schematic diagram showing a blood pressure and heart rate measuring device according to a fourth embodiment of the present invention.

FIG. 6 is a schematic diagram showing a blood pressure and heart rate measuring device according to a fourth embodiment of the present invention. The blood pressure and heart rate measuring device of FIG. 5 is almost the same as that of FIG. 6. Their difference is that the blood pressure and heart rate measuring device 30' of FIG. 6 further includes a second photo receiver 37 connected to the second optical coupler 33*b* through an eighth optical path 38*h*. When the optical power of the broadband light source 32 is unstable, the optical power of the eighth light ray L28 received by the first photo receiver 34 will also be unstable, which may distort the finally obtained pulse waveform. The blood pressure and heart rate measuring device 30' employs the second photo receiver 37 to improve the problem. Specifically, after the second optical coupler 33*b* receives the fifth light ray L25, the second optical coupler 33*b* will generate a ninth light ray L29 and transmit the ninth light ray L29 to the second photo receiver 37 through the eighth optical path 38*h*. The second photo receiver 37 generates a second electrical signal in response to the ninth light ray L29. Since the first electrical signal and the second electrical signal both include unstable components of the broadband light source 32, the blood pressure and heart rate measuring device 30' can cancel out the unstable components when dividing the first electrical signal by the second electrical signal. In other words, the pulsating waveform signal obtained by dividing the first electrical signal by the second electrical signal excludes the unstable component and will not be affected by the instability of the broadband light source 32.

Figure 7:
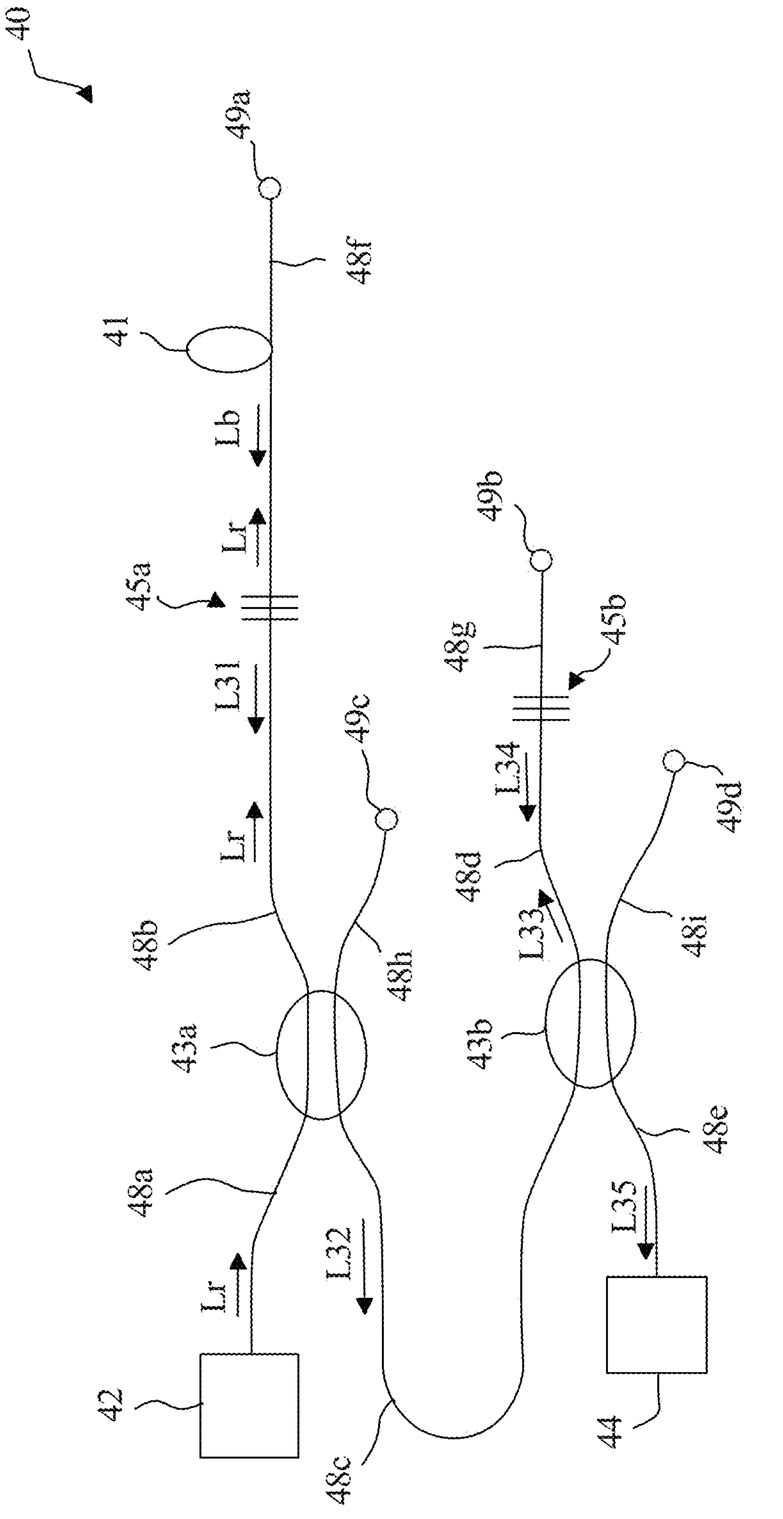
FIG. 7 is a schematic diagram showing a blood pressure and heart rate measuring device according to a fifth embodiment of the present invention.

FIG. 7 is a schematic diagram showing a blood pressure and heart rate measuring device according to a fifth embodiment of the present invention. The blood pressure and heart rate measuring device 40 of FIG. 7 includes at least an erbium (Er)-doped fiber 41, a laser light source 42, a first optical coupler 43*a*, a second optical coupler 43*b*, a first photo receiver 44, a first fiber grating 45*a*, and a second fiber grating 45*b*. The laser light source 42 provides laser light Lr for the first optical coupler 43*a* through a first optical path 48*a*. The first optical coupler 43*a* has a wavelength division multiplexing function. The first optical coupler 43*a* guides the laser light Lr to a second optical path 48*b*, so that the laser light Lr is emitted to the first fiber grating 45*a* through the second optical path 48*b*. The first fiber grating 45*a* has a first reflection wavelength band RB1 and a first transmission wavelength band TB1. The laser light Lr passes through the first fiber grating 45*a* and enters the erbium-doped fiber 41. The erbium-doped fiber 41 generates broadband light Lb in response to the laser light Lr and transmits the broadband light Lb back to the first fiber grating 45*a*. The central wavelength of the broadband light Lb ranges between 1500 nm and 1590 nm. The part of the broadband light Lb whose wavelength band is within the first transmission wavelength band TB1 will pass through the first fiber grating 45*a* to generate a first light ray L31. The first light ray L31 is emitted to the first optical coupler 43*a* along the second optical path 48*b*. The first optical coupler 43*a* generates a second light ray L32 in response to the first light ray L31. The second light L32 is provided to the second optical coupler 43*b* through a third optical path 48*c*. The second optical coupler 43*b* generates a third light ray L33 in response to the second light ray L32 and transmits the third light ray L33 to the second fiber grating 45*b* along a fourth optical path 48*d*. The second fiber grating 45*b* has a second reflection wavelength band RB2 and a second transmission wavelength band TB2. The part of the third light ray L33 whose wavelength band is within the second reflection wavelength band RB2 is reflected by the second fiber grating 45*b* to generate a fourth light ray L34. The fourth light ray L34 returns to the second optical coupler 43*b* along the fourth optical path 48*d*. The second optical coupler 43*b* generates a fifth light ray L35 in response to the fourth light ray L34 and transmits the fifth light ray L35 to the first photo receiver 44 along a fifth optical path 48*e*. The first photo receiver 44 generates a first electrical signal of the pulse waveform of vascular pulsation based on the optical power of the fifth light ray L35, wherein the first electrical signal is converted into a current signal or a voltage signal. The fifth light ray L35 has a wavelength band within the overlapping wavelength band of the first transmission wavelength band TB1 and the second reflection wavelength band RB2.

In FIG. 7, the second fiber grating 45*b* is adjacent to the surface of an object to be measured (such as human skin). Thus, the second fiber grating 45*b* will shift the second reflection wavelength band RB2 and the second transmission wavelength band TB2 due to the vascular pulsating stress. Since the first fiber grating 45*a* is far away from the surface of the object to be measured, the first fiber grating 45*a* is less or not affected by the vascular pulsating stress. Therefore, the first reflection wavelength band RB1 and the first transmission wavelength band TB1 of the first fiber grating 45*a* will only shift slightly or not shift at all. When the second fiber grating 45*b* bears the vascular pulsating stress, the second reflection wavelength band RB2 shifts with vascular pulsation, which changes the area of the overlapping wavelength band of the first transmission wavelength band TB1 and the second reflection wavelength band RB2. In other words, the optical power of the fifth light ray L35 received by the first photo receiver 44 changes with the vascular pulsation. Thus, the optical power received by the first photo receiver 44 presents a pulse waveform signal.

In FIG. 7, the blood pressure and heart rate measuring device 40 further includes a sixth optical path 48*f*, a seventh optical path 48*g*, an eighth optical path 48*h*, and a ninth optical path 48*i* respectively connected to the Er-doped fiber 41, the second fiber grating 45*b*, the first optical coupler 43*a*, and the second optical coupler 43*b*. In order to avoid Fresnel reflections at the end surfaces 49*a*, 49*b*, 49*c*, and 49*d* of the sixth optical path 48*f*, the seventh optical path 48*g*, the eighth optical path 48*h*, and the ninth optical path 49*i*, there are several ways to avoid reflecting light rays back into the optical paths: (1) coating anti-reflective materials on the end surfaces 49*a*, 49*b*, 49*c*, and 49*d*; (2) designing the end faces 49*a*, 49*b*, 49*c*, and 49*d* to have an inclination angle greater than 3 degrees; and (3) designing the optical paths near the end faces 49*a*, 49*b*, 49*c*, and 49*d* to have curled shapes with small radiuses of curvature to produce the bending loss of light.

The first optical path 48*a*, the second optical path 48*b*, the third optical path 48*c*, the fourth optical path 48*d*, the fifth optical path 48*e*, the sixth optical path 48*f*, the seventh optical path 48*g*, the eighth optical path 48*h*, and the ninth optical 48*i* in FIG. 7 can be fiber optical paths, waveguide optical paths, or fiber and waveguide mixed optical paths.

Figure 8:
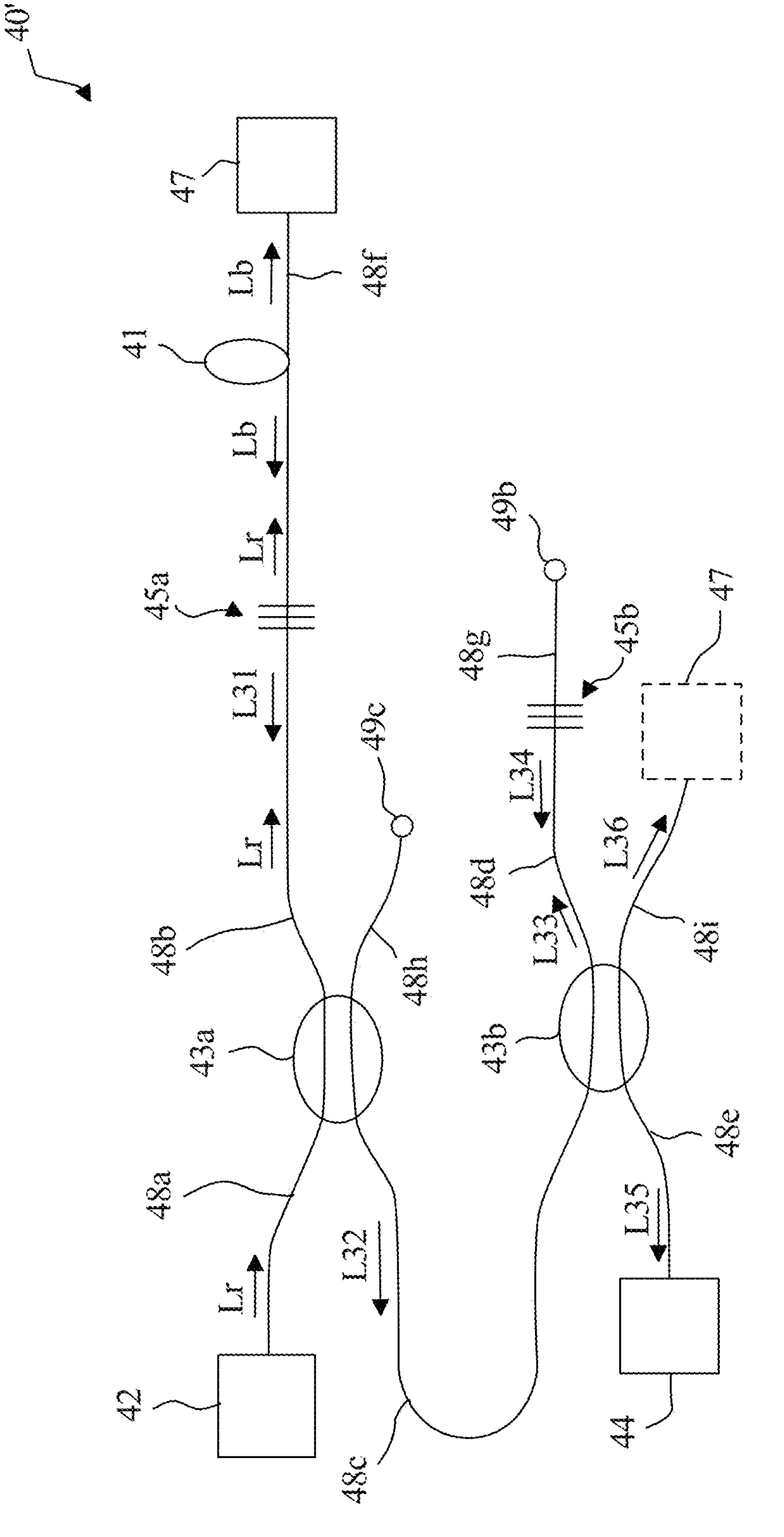
FIG. 8 is a schematic diagram showing a blood pressure and heart rate measuring device according to a sixth embodiment of the present invention.

FIG. 8 is a schematic diagram showing a blood pressure and heart rate measuring device according to a sixth embodiment of the present invention. The blood pressure and heart rate measuring device of FIG. 7 is almost the same as that of FIG. 8. Their difference is that the blood pressure and heart rate measuring device 40' of FIG. 8 further includes a second photo receiver 47 connected to the Er-doped fiber 41 through the sixth optical path 48*f* or connected to the second optical coupler 43*b* through the ninth optical path 48*i*. When the optical power of the Er-doped fiber 41 is unstable, the optical power of the fifth light ray L35 received by the first photo receiver 44 will also be unstable, which may distort the finally obtained pulse waveform.

The blood pressure and heart rate measuring device 40' employs the second photo receiver 47 to improve the problem. Specifically, after the second photo receiver 47 receives a broadband light Lb through the sixth optical path 48*f* or receives the sixth light ray L36 through the ninth optical path 48*i*, the second photo receiver 47 will generate a second electrical signal in response to the broadband light Lb or the sixth light ray L36. Since the first electrical signal and the second electrical signal both include unstable components of the broadband light Lb, the blood pressure and heart rate measuring device 40' can cancel out the unstable components when dividing the first electrical signal by the second electrical signal. In other words, the pulsating waveform signal obtained by dividing the first electrical signal by the second electrical signal excludes the unstable component and will not be affected by the instability of the broadband light Lb.

Figure 9:
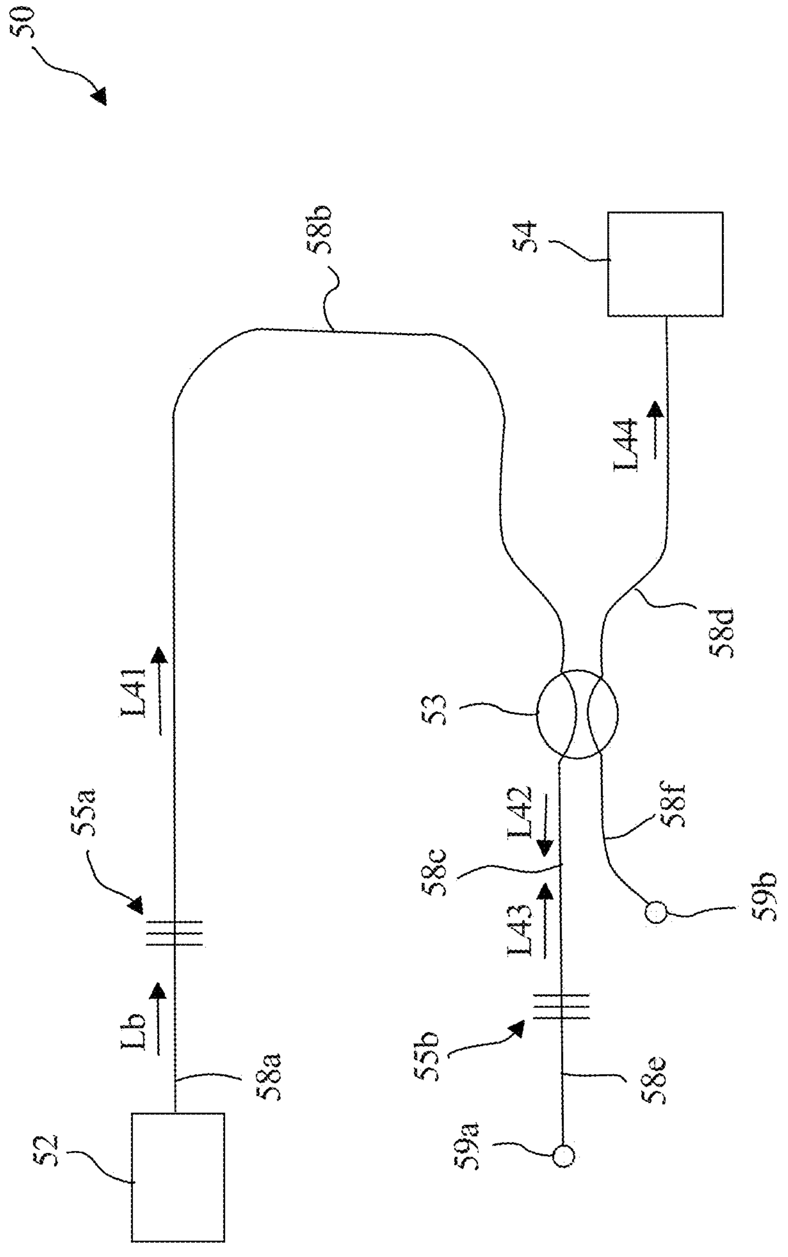
FIG. 9 is a schematic diagram showing a blood pressure and heart rate measuring device according to a seventh embodiment of the present invention.

FIG. 9 is a schematic diagram showing a blood pressure and heart rate measuring device according to a seventh embodiment of the present invention. The blood pressure and heart rate measuring device 50 of FIG. 9 includes at least a broadband light source 52, an optical coupler 53, a first photo receiver 54, a first fiber grating 55*a*, and a second fiber grating 55*b*. The broadband light source 52 provides broadband light Lb for the first fiber grating 55*a* through a first optical path 58*a*. The first fiber grating 55*a* has a first reflection wavelength band RB1 and a first transmission wavelength band TB1. The part of the broadband light Lb whose wavelength band is within the first transmission wavelength band TB1 will pass through the first fiber grating 55*a* to generate a first light ray L41. The first light ray L41 enters the optical coupler 53 along a second optical path 58*b*. The optical coupler 53 generates a second light ray L42 in response to the first light ray L41 and transmits the second light ray L42 to the second fiber grating 55*b* through a third optical path 58*c*, where the second light ray L42 is a part or all of the first light ray L41. The second fiber grating 55*b* has a second reflection wavelength band RB2 and a second transmission wavelength band TB2. The part of the second light ray L42 whose wavelength band is within the second reflection wavelength band RB2 is reflected by the second fiber grating 55*b* to generate a third light ray L43 that returns to the optical coupler 53 along the third optical path 58*c*. The optical coupler 53 generates a fourth light ray L44 in response to the third light ray L43 and provides the fourth light ray L44 for the first photo receiver 54 through a fourth optical path 58*d*. The first photo receiver 54 generates a first electrical signal of the pulse waveform of vascular pulsation based on the optical power of the fourth light ray L44, wherein the first electrical signal is converted into a current signal or a voltage signal.

In FIG. 9, the second fiber grating 55*b* is adjacent to the surface of an object to be measured (such as human skin). Thus, the second fiber grating 55*b* will shift the second reflection wavelength band RB2 and the second transmission wavelength band TB2 due to the vascular pulsating stress. Since the first fiber grating 55*a* is far away from the surface of the object to be measured, the first fiber grating 55*a* is less or not affected by the vascular pulsating stress. Therefore, the first reflection wavelength band RB1 and the first transmission wavelength band TB1 of the first fiber grating 55*a* will only shift slightly or not shift at all. When the second fiber grating 55*b* bears the vascular pulsating stress, the second reflection wavelength band RB2 shifts with vascular pulsation, which changes the area of the overlapping wavelength band of the first transmission wavelength band TB1 and the second reflection wavelength band RB2. In other words, the optical power of the fourth light ray L44 received by the first photo receiver 54 changes with the vascular pulsation. Thus, the optical power received by the first photo receiver 54 presents a pulse waveform signal.

In FIG. 9, the blood pressure and heart rate measuring device 50 further includes a fifth optical path 58*e* and a sixth optical path 58*f* respectively connected to the fiber grating 55*b* and the optical coupler 53. In order to avoid Fresnel reflections at the end surfaces 59*a* and 59*b* of the fifth optical path 58*e* and the sixth optical path 58*f*, there are several ways to avoid reflecting light rays back into the optical paths: (1) coating anti-reflective materials on the end surfaces 59*a* and 59*b*; (2) designing the end faces 59*a* and 59*b* to have an inclination angle greater than 3 degrees; and (3) designing the optical paths near the end faces 59*a* and 59*b* to have curled shapes with small radiuses of curvature to produce the bending loss of light.

The first optical path 58*a*, the second optical path 58*b*, the third optical path 58*c*, the fourth optical path 58*d*, the fifth optical path 58*e*, and the sixth optical path 58*f* in FIG. 9 can be fiber optical paths, waveguide optical paths, or fiber and waveguide mixed optical paths.

Figure 10:
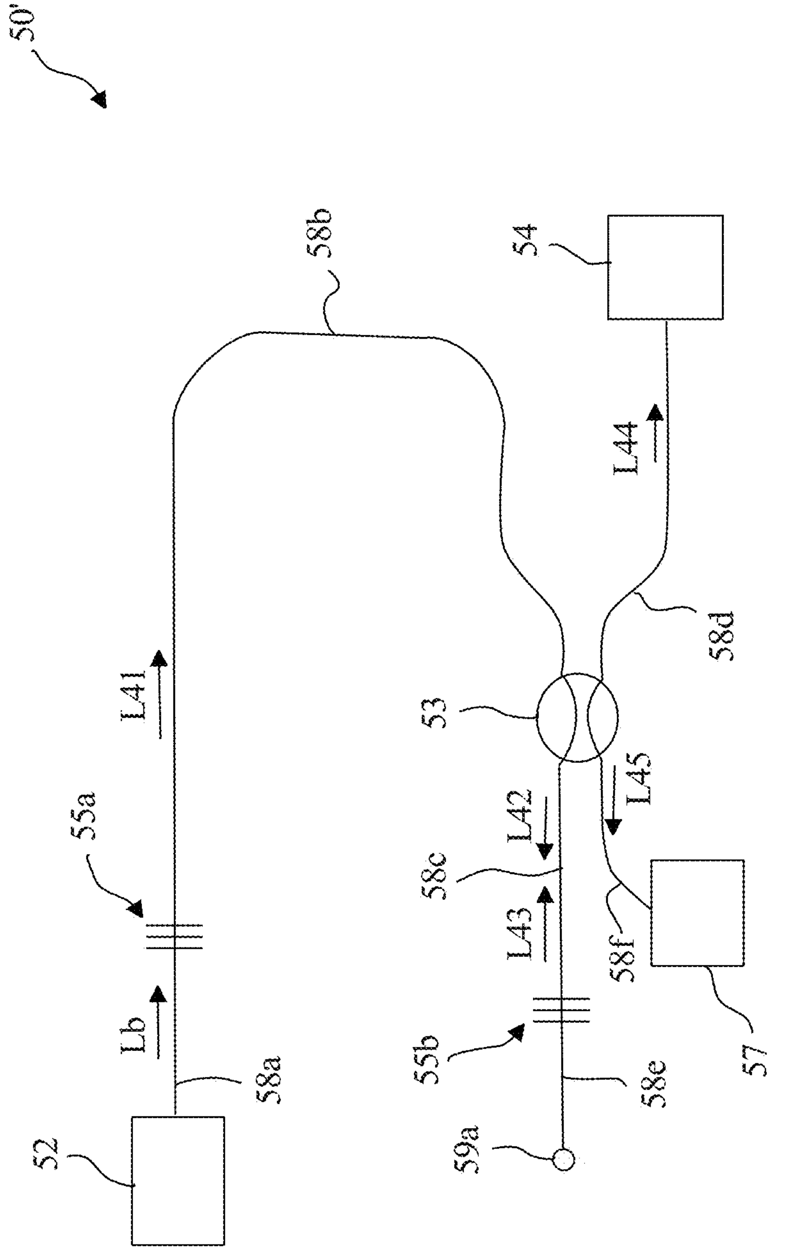
FIG. 10 is a schematic diagram showing a blood pressure and heart rate measuring device according to an eighth embodiment of the present invention.

FIG. 10 is a schematic diagram showing a blood pressure and heart rate measuring device according to an eighth embodiment of the present invention. The blood pressure and heart rate measuring device of FIG. 9 is almost the same as that of FIG. 10. Their difference is that the blood pressure and heart rate measuring device 50' of FIG. 10 further includes a second photo receiver 57 connected to the optical coupler 53 through the sixth optical path 58*f*. When the optical power of the broadband light source 52 is unstable, the optical power of the fourth light ray L44 received by the first photo receiver 54 will also be unstable, which may distort the finally obtained pulse waveform. The blood pressure and heart rate measuring device 50' employs the second photo receiver 57 to improve the problem. Specifically, after the optical coupler 53 receives the first light ray L41, the optical coupler 53 will generate a fifth light ray L45 and transmits the fifth light ray L45 to the second photo receiver 57 through the sixth optical path 58*f*. The second photo receiver 57 generates a second electrical signal in response to the fifth light ray L45. Since the first electrical signal and the second electrical signal both include unstable components of the broadband light source 52, the blood pressure and heart rate measuring device 50' can cancel out the unstable components when dividing the first electrical signal by the second electrical signal. In other words, the pulsating waveform signal obtained by dividing the first electrical signal by the second electrical signal excludes the unstable component and will not be affected by the instability of the broadband light source 52.

Figure 11:
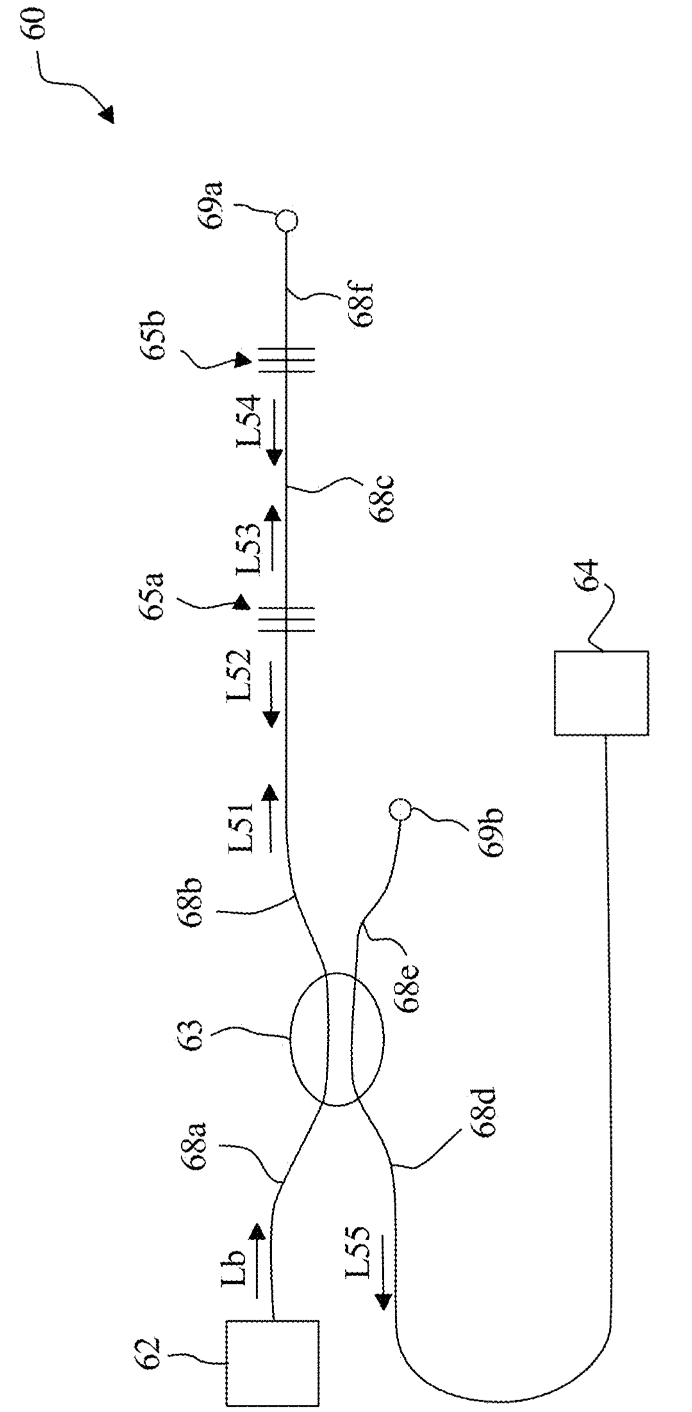
FIG. 11 is a schematic diagram showing a blood pressure and heart rate measuring device according to a ninth embodiment of the present invention.

FIG. 11 is a schematic diagram showing a blood pressure and heart rate measuring device according to a ninth embodiment of the present invention. The blood pressure and heart rate measuring device 60 of FIG. 11 includes at least a broadband light source 62, an optical coupler 63, a first photo receiver 64, a first fiber grating 65*a*, and a second fiber grating 65*b*. The broadband light source 62 provides broadband light Lb for the optical coupler 63 through a first optical path 68*a*. The optical coupler 63 generates a first light ray L51 in response to the broadband light Lb and transmits the first light ray L51 to the first fiber grating 65*a* through a second optical path 68*b*, where the first light ray L51 is a part or all of the broadband light Lb. The first fiber grating 65*a* has a first reflection wavelength band RB1 and a first transmission wavelength band TB1. The part of the first light ray L51 whose wavelength band is within the first reflection wavelength band RB1 will be reflected by the first fiber grating 65*a* to generate a second light ray L52 that returns to the optical coupler 63 along the second optical path 68*b*. The part of the first light ray L51 whose wavelength band is within the first transmission wavelength band TB1 will pass through the first fiber grating 65*a* to generate a third light ray L53 that is emitted to the second fiber grating 65*b* along a third optical path 68*c*. The second fiber grating 65*b* has a second reflection wavelength band RB2 and a second transmission wavelength band TB2. The part of the third light ray L53 whose wavelength band is within the second reflection wavelength band RB2 is reflected by the second fiber grating 65*b* to form a fourth light ray L54 that returns to the optical coupler 63 through the third optical path 68*c*, the first fiber grating 65*a*, and the second optical path 68*b*. After receiving the second light ray L52 and the fourth light ray L54, the optical coupler 63 generates a fifth light ray L55 and provides it for the first photo receiver 64 along a fourth optical path 68*d*, where the fifth light ray L55 is a part or all of the sum of the second light ray L52 and the fourth light ray L54. The first photo receiver 64 generates a first electrical signal of the pulse waveform of vascular pulsation based on the optical power of the fifth light ray L55, wherein the first electrical signal is converted into a current signal or a voltage signal.

In FIG. 11, the first fiber grating 65*a* or the second fiber grating 65*b* is adjacent to the surface of an object to be measured (such as human skin). Thus, the fiber grating adjacent to the surface of an object to be measured will shift the reflection wavelength band and the transmission wavelength band due to the vascular pulsating stress. The fiber grating, which is far away from the surface of the object to be measured, is less or not affected by the vascular pulsating stress. Therefore, the reflection wavelength band and the transmission wavelength band will only shift slightly or not shift at all. When the first fiber grating 65*a* or the second fiber grating 65*b* adjacent to the surface of an object to be measured bears the vascular pulsating stress, the area of the union of the first reflection wavelength band RB1 and the second reflection wavelength band RB2 changes with the vascular pulsating stress. In other words, the optical power of the fifth light ray L55 received by the first photo receiver 64 changes with the vascular pulsation. Thus, the optical power received by the first photo receiver 64 presents a pulse waveform signal.

In FIG. 11, the blood pressure and heart rate measuring device 60 further includes a fifth optical path 68*e* and a sixth optical path 68*f* respectively connected to the optical coupler 63 and the second fiber grating 65*b*. In order to avoid Fresnel reflections at the end surfaces 69*a* and 69*b* of the fifth optical path 68*e* and the sixth optical path 68*f*, there are several ways to avoid reflecting light rays back into the optical paths: (1) coating anti-reflective materials on the end surfaces 69*a* and 69*b*; (2) designing the end faces 69*a* and 69*b* to have an inclination angle greater than 3 degrees; and (3) designing the optical paths near the end faces 69*a* and 69*b* to have curled shapes with small radiuses of curvature to produce the bending loss of light.

The first optical path 68*a*, the second optical path 68*b*, the third optical path 68*c*, the fourth optical path 68*d*, the fifth optical path 68*e*, and the sixth optical path 68*f* in FIG. 11 can be fiber optical paths, waveguide optical paths, or fiber and waveguide mixed optical paths.

Figure 12:
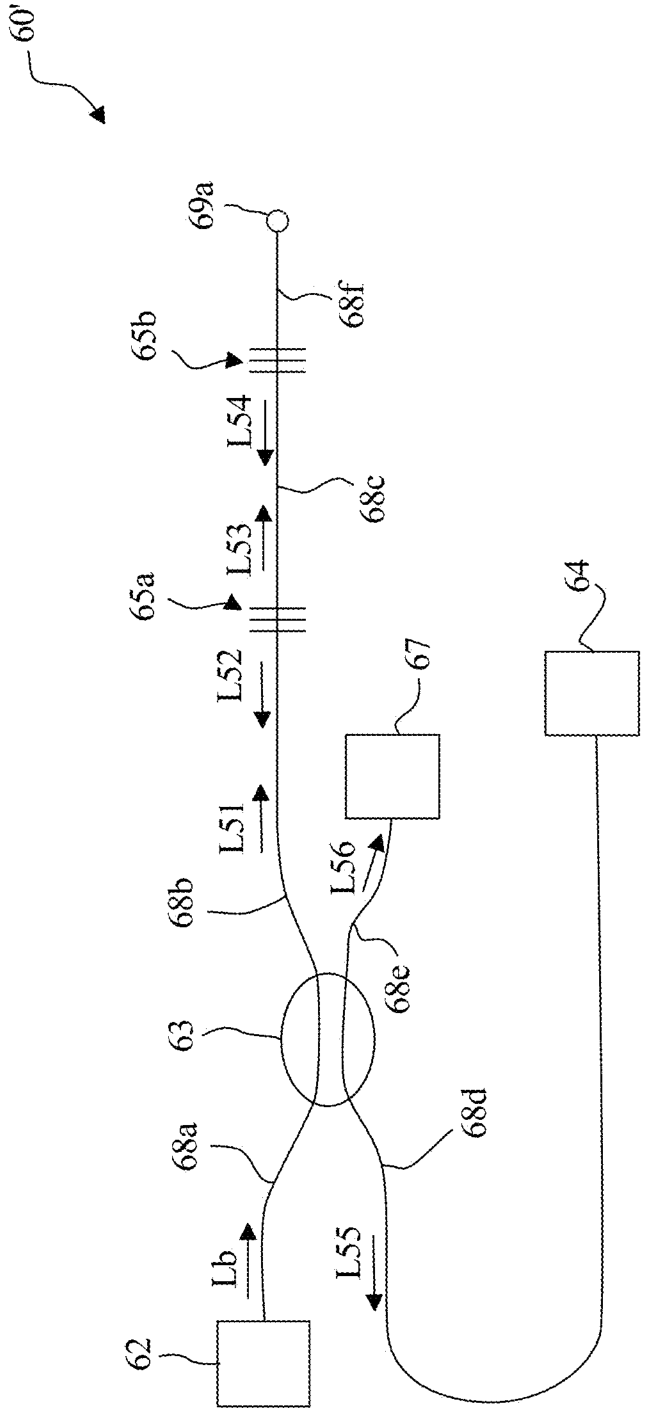
FIG. 12 is a schematic diagram showing a blood pressure and heart rate measuring device according to a tenth embodiment of the present invention.

FIG. 12 is a schematic diagram showing a blood pressure and heart rate measuring device according to a tenth embodiment of the present invention. The blood pressure and heart rate measuring device of FIG. 11 is almost the same as that of FIG. 12. Their difference is that the blood pressure and heart rate measuring device 60' of FIG. 12 further includes a second photo receiver 67 connected to the optical coupler 63 through the fifth optical path 68*e*. When the optical power of the broadband light source 62 is unstable, the optical power of the fifth light ray L55 received by the first photo receiver 64 will also be unstable, which may distort the finally obtained pulse waveform. The blood pressure and heart rate measuring device 60' employs the second photo receiver 67 to improve the problem. Specifically, after the optical coupler 63 receives the broadband light Lb, the optical coupler 63 will generate a sixth light ray L56 and transmits the sixth light ray L56 to the second photo receiver 67 through the fifth optical path 68*e*. The second photo receiver 67 generates a second electrical signal in response to the sixth light ray L56. Since the first electrical signal and the second electrical signal both include unstable components of the broadband light source 62, the blood pressure and heart rate measuring device 60' can cancel out the unstable components when dividing the first electrical signal by the second electrical signal. In other words, the pulsating waveform signal obtained by dividing the first electrical signal by the second electrical signal excludes the unstable component and will not be affected by the instability of the broadband light source 62.

Figure 13:
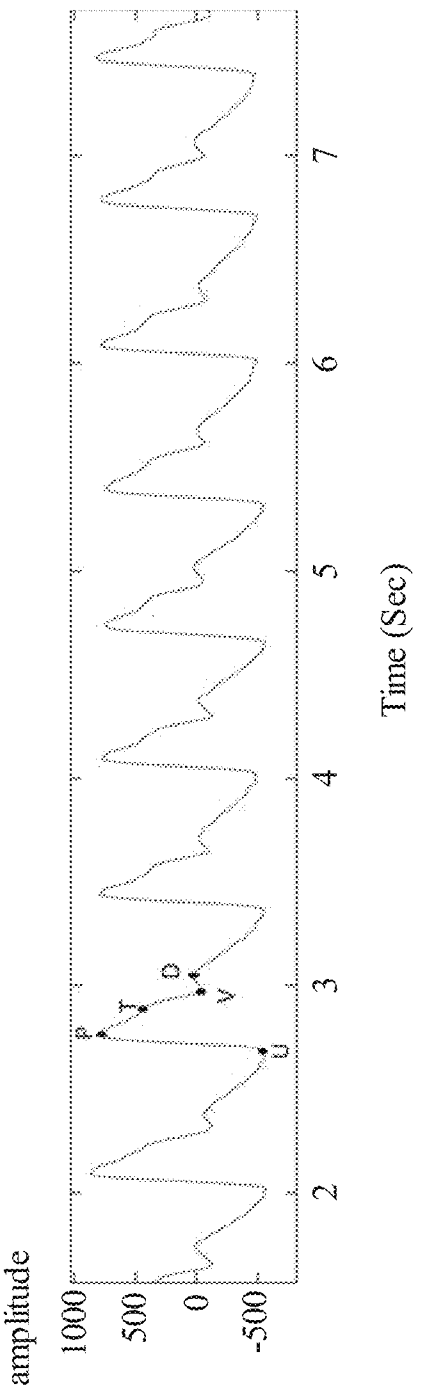
FIG. 13 is a schematic diagram showing a pulse waveform signal obtained by a blood pressure and heart rate measuring device.
Figure 14:
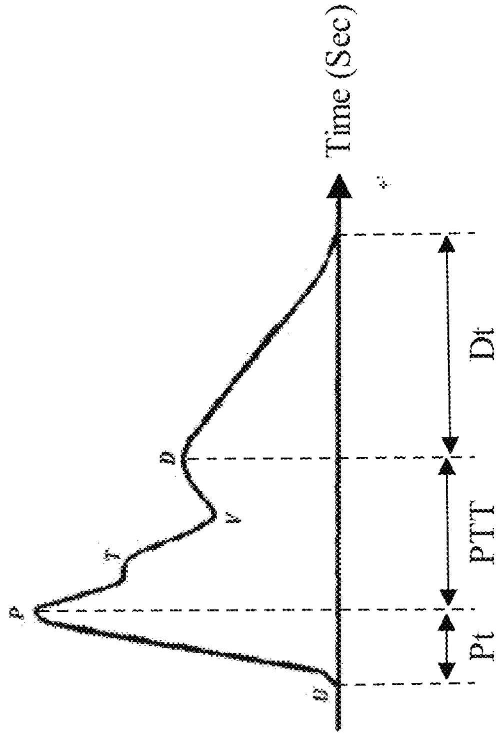
FIG. 14 is an enlarged view of a part of the pulse waveform signal in FIG. 13.

FIG. 13 is a schematic diagram showing a pulse waveform signal obtained by a blood pressure and heart rate measuring device. FIG. 14 is an enlarged view of a part of the pulse waveform signal in FIG. 13. FIG. 13 shows the filtered pulse waveform signal for retaining signal components ranging from, for example, 0.5 Hz to 12 Hz. In FIG. 13 and FIG. 14, the time interval between point P and point D is defined as PTT. The time interval from point U (i.e., an onset point) of the pulse waveform to point P (i.e., a main wave peak point) is defined as Pt. The time interval from point D (i.e., a dicrotic wave peak point) to the end point of the pulse waveform that is normally the onset point of the next pulse waveform, is defined as Dt. The heart rate can be obtained from the repetition rate of the pulse waveform signal in FIG. 13. In other words, the heart rate can be obtained from the repetition rate of point U, point P, point V (i.e., a descending wave trough point) or point D of the pulse waveform. A systolic blood pressure (SBP) and a diastolic blood pressure (DBP) can be calculated using the three parameters PTT, Pt and Dt of the pulse waveform signal and the following formula 1 and formula 2.

$$SBP = A \times \ln(PTT) + \frac{C}{(PTT)^2} + E \times Pt + G \quad (1)$$

$$DBP = B \times \ln(PTT) + \frac{D}{(PTT)^2} + F \times Dt + H \quad (2)$$

In formula 1 and formula 2, In is a natural logarithmic function, the value of coefficient A ranges between 300 and 900, the value of coefficient B ranges between 600 and 950, the value of coefficient C ranges between 2 and 50, the value of coefficient D ranges between 5 and between 50, the value of coefficient E ranges between 4 and 60, the value of coefficient F ranges between −25 and 50, the value of constant G ranges between 450 and 850, and the value of constant H ranges between 600 and 900.

Because the processed pulse waveform signal has multiple P-point peaks within a period of time and the three time parameters PTT, Pt and Dt provided by the pulse waveforms of these different peaks will be different, it is necessary to use the averaging method to obtain these time parameters. The averaging method is divided into two types. One type is to take out the time parameters of each pulse waveform and then average the time parameters of these pulse waveforms. Another type is to average the waveform values of these pulse waveforms at corresponding time points to obtain an average pulse waveform and then extract each time parameter from the average pulse waveform.

The deviation between the 3 dB bandwidths of the reflection spectrums of the two fiber gratings used by the blood pressure and heart rate measuring method of the present invention is less than 2 nm. The deviation between the central values of the reflection wavelengths of the reflection spectrums of the two fiber gratings used by the blood pressure and heart rate measuring method of the present invention is less than 3 nm. The broadband light source of the present invention has a 3 dB bandwidth between 2 nm and 800 nm and has a central wavelength within the wavelength range of visible light or infrared light. The broadband light source of the present invention may be, but not limited to, a light emitting diode (LED), a semiconductor optical amplifier, a semiconductor superluminescent diode, or a pumped erbium-doped fiber.

The blood pressure and heart rate measuring device of the present invention uses two fiber gratings to measure and obtain pulse waveform signals. One of the fiber gratings bears vascular pulsation to deform the fiber grating and shift its reflection wavelength band, thereby changing the optical power detected by the photo receiver to obtain a pulse waveform signal. Fiber gratings, which serve as the pulsating sensors of blood vessels, must be close to the blood vessels. However, in order to prevent the fiber grating and the adjacent fiber optical path from being damaged or broken when placing and moving the blood pressure and heart rate measuring device, the optical fiber grating and the adjacent fiber optical path are placed in a stretchable material and the fiber grating is close to the skin next to the brachial artery of the upper arm or the skin next to the radial artery of the lower arm to obtain the pulse waveform signal.

Figure 15:
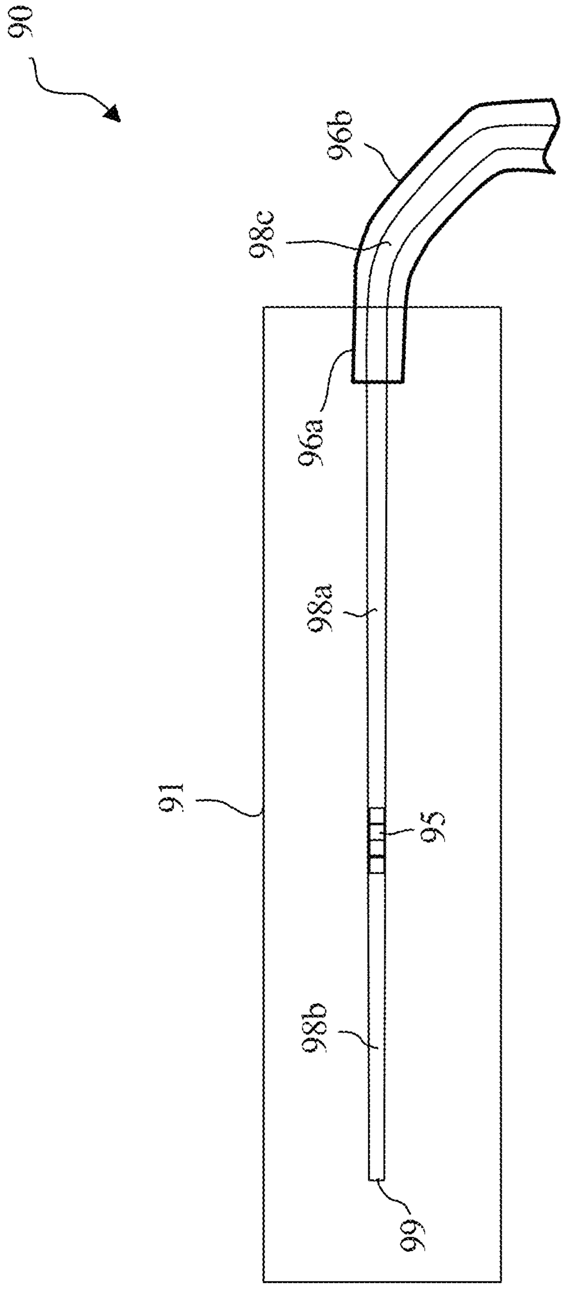
FIG. 15 is a schematic diagram showing a protective structure for protecting a fiber grating and a fiber optical path adjacent thereto.

FIG. 15 is a schematic diagram showing a protective structure for protecting a fiber grating and a fiber optical path adjacent thereto. In the protective structure 90 of FIG. 15, a fiber grating 95, the adjacent fiber optical paths 98*a* and 98*b*, and a portion of the fiber optical path 98*c* are placed in the stretchable material 91, wherein the end face 99 of the fiber optical path 98*b* has an inclined angle of more than 3 degrees. Alternatively, a part of the fiber optical path in front of the end face has a bending loss of light and presents a curled state with a small radius of curvature or the end face is coated with an anti-reflective material. The fiber optical path 98*c* is divided into two parts respectively placed in a tube 96*a* and a tube 96*b*. The tube 96*a* and the fiber optical path 98*c* therein are placed in the stretchable material 91. The light ray can be emitted to the fiber grating 95 from the fiber optical path 98*c* outside the stretchable material 91 through the fiber optical path 98*c* and the fiber optical path 98*a* inside the stretchable material 91. Then, the light ray whose wavelength band is in the reflection wavelength band of the fiber grating 95 is reflected along the fiber optical paths 98*a* and 98*c*. The light ray is finally transmitted to the photo receiver to obtain the pulse waveform signal. The heart rate, the systolic blood pressure, and the diastolic blood pressure are calculated using the foregoing method.

Figure 16:
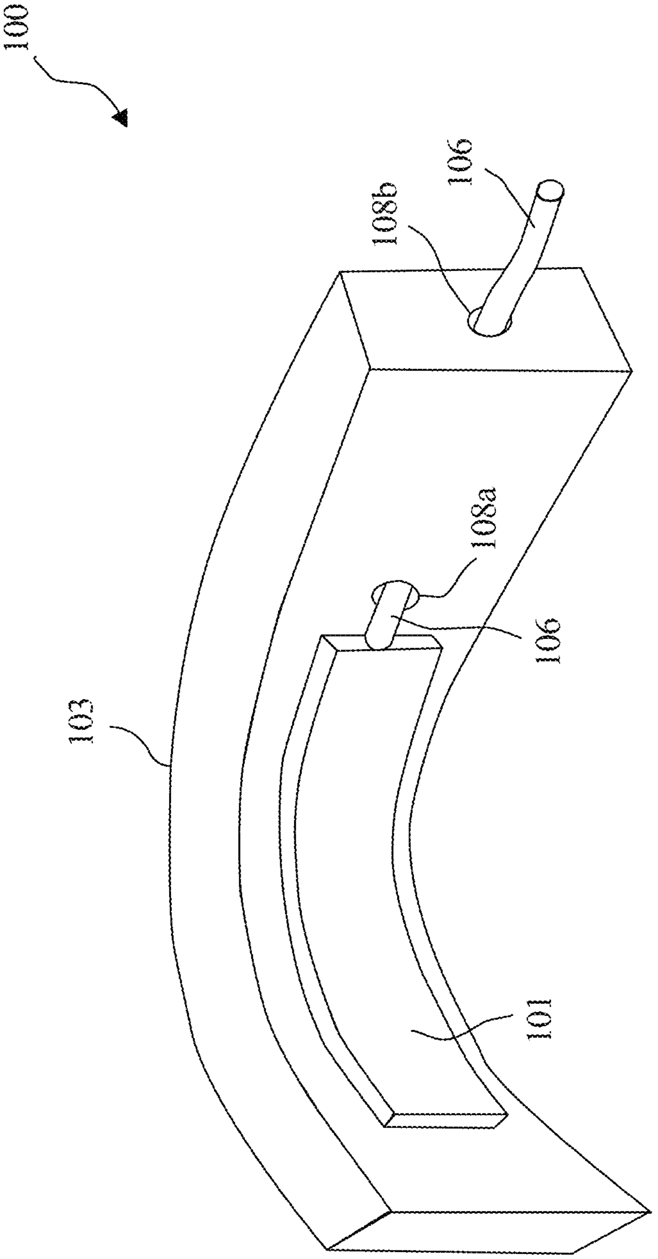
FIG. 16 is a schematic diagram showing the arm belt of a blood pressure and heart rate measuring device.

FIG. 16 is a schematic diagram showing the arm belt 100 of a blood pressure and heart rate measuring device. The arm belt 100 can surround the object to be measured (such as a human arm) to measure a blood pressure and a heart rate. In order to display the heart rate, the systolic blood pressure and the diastolic blood pressure obtained by the blood pressure and heart rate measuring device of the present invention and to conveniently measure the heart rate, the systolic blood pressure and the diastolic blood pressure, a preferred example of the present invention uses a box with a displaying function. The box has a function of displaying at least a heart rate, a systolic blood pressure, and a diastolic blood pressure. Besides, in the box there are at least a fiber, an erbium-doped fiber, an optical coupler, a semiconductor light source, an photo receiver, a power supply, a power switch, a circuit board, an integrated circuit including a heart rate/systolic blood calculation program for calculating pressure/diastolic blood pressure, a switch for selecting functional operations, and at most one fiber grating. The device inside the box is connected to the stretchable material 101 of the arm belt 100 in FIG. 16 by one strip-shaped object 106 that includes at least a fiber optical path. The purpose of the strip-shaped object 106 is to protect the fiber optical path that is connected to the fiber grating inside the stretchable material. Specifically, the strip-shaped object 106 can be the tube 96*b* in FIG. 15 or another flexible object covering the tube. The strip-shaped object 106 at least includes the fiber optical path 98*c*, as shown in FIG. 15. The stretchable material 101 is secured to one surface of a girdle 103. The internal structure of the stretchable material 101 may refer to the stretchable material 91 in FIG. 15. The girdle 103 includes holes 108*a* and 108*b* where the strip-shaped object 106 passes. Practically, all or a part of the arm belt 100 surrounds the suitable position of the arm, so that the fiber grating in the arm belt 100 can sense the pulsation of blood vessels. In another preferred example, the box also includes a module with signal transmission function.

Figure 17:
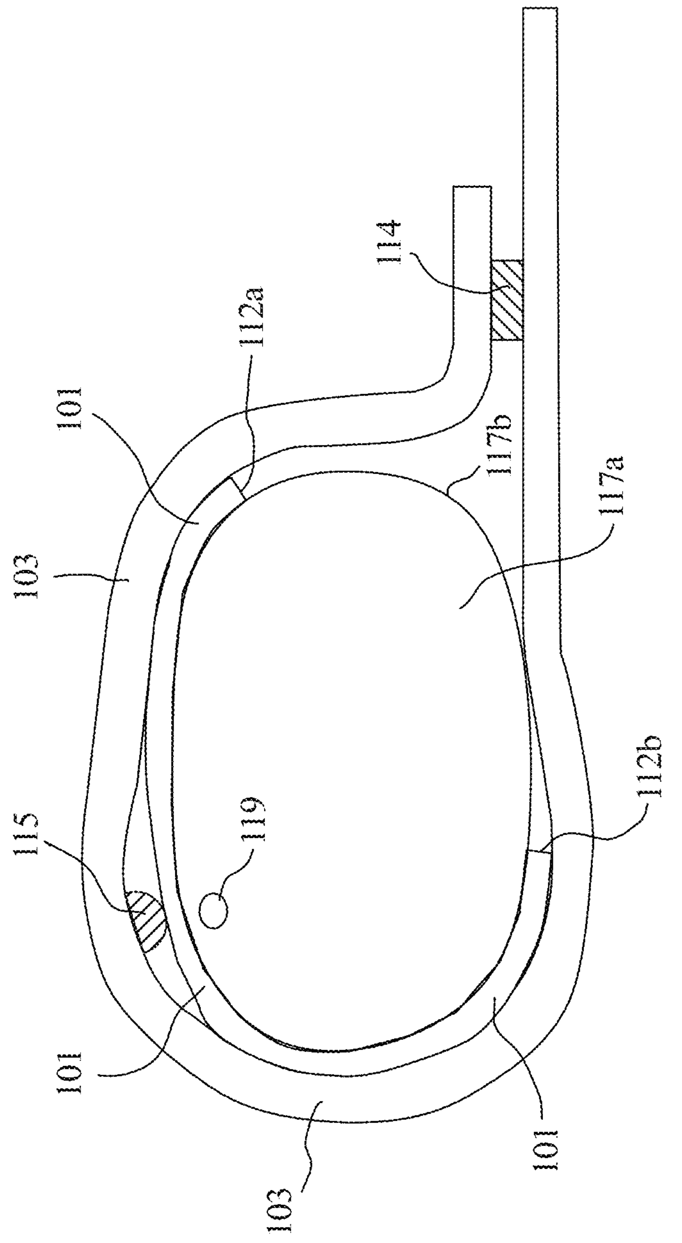
FIG. 17 is a cross-sectional view of an arm belt in FIG. 16 that surrounds an arm.

FIG. 17 is a cross-sectional view of an arm belt in FIG. 16 that surrounds an arm. In FIG. 17, a stretchable material 101 including a fiber optical path and a fiber grating is secured to one surface of the girdle 103. A force-applying body 115 is located between the stretchable material 101 and the girdle 103. The force-applying body 115 has a U-shaped or arc-shaped structure. The former has its opening facing toward the stretchable material 101 and the latter has an arc-shaped surface facing toward the stretchable material 101. When the girdle 103 surrounds an arm 117*a*, the force-applying body 115 applies force to the stretchable material 101, so that the stretchable material 101 closely contacts the local area of an arm skin 117*b*. Thus, the pulsation of the blood vessel 119 can be sensed by the fiber grating inside the stretchable material 101, wherein the fiber grating is located near the blood vessel 119. The girdle 103 has an adhesive member 114 that can join the two ends of the girdle 103. The fiber optical path in the stretchable material 101 extends from the end surface 112*a* or 112*b* of the stretchable material 101 and then passes through the girdle 103.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A blood pressure and heart rate measuring device comprising at least:

a broadband light source configured to provide broadband light;

an optical coupler connected to the broadband light source through a first optical path and configured to receive the broadband light;

a first fiber grating, connected to the optical coupler through a second optical path, having a first reflection wavelength band, wherein the first fiber grating is configured to receive a first light ray from the optical coupler through the second optical path and reflect a part of the first light ray whose wavelength band is within the first reflection wavelength band to generate a second light ray that returns to the optical coupler along the second optical path, and the first light ray is a part or all of the broadband light;

a second fiber grating, connected to the optical coupler through a third optical path, having a second reflection wavelength band, wherein the second fiber grating is configured to receive a third light ray from the optical coupler through the third optical path and allow a part of the third light ray whose wavelength band is not within the second reflection wavelength band to pass to generate a fourth light ray, and the third light ray is a part or all of the second light ray; and a first photo receiver connected to the second fiber grating through a fourth optical path and configured to receive the fourth light ray from the second fiber grating through the fourth optical path and generate a first electrical signal of a pulse waveform of vascular pulsation in response to the fourth light ray;

wherein the first reflection wavelength band shifts with a vascular pulsating stress of an object to be measured.

2. The blood pressure and heart rate measuring device according to claim 1, further comprising a second photo receiver configured to receive a fifth light ray from the optical coupler through a fifth optical path and generate a second electrical signal in response to the fifth light ray, wherein the blood pressure and heart rate measuring device is configured to divide the first electrical signal by the second electrical signal to obtain a pulsating waveform signal, and the fifth light ray is a part or all of the broadband light.

3. The blood pressure and heart rate measuring device according to claim 1, wherein a deviation between 3 dB bandwidths of the first reflection wavelength band and the second reflection wavelength band is less than 2 nm and a deviation between central values of reflection wavelengths of the first reflection wavelength band and the second reflection wavelength band is less than 3 nm.

4. The blood pressure and heart rate measuring device according to claim 1, wherein a 3 dB bandwidth of the broadband light source ranges between 2 nm and 800 nm and a central wavelength of the broadband light source is within a wavelength range of visible light or infrared light.

5. A blood pressure and heart rate measuring device comprising at least:

a broadband light source configured to provide broadband light;

a first optical coupler connected to the broadband light source through a first optical path and configured to receive the broadband light, wherein the first optical coupler is configured to generate a first light ray and a second light ray in response to the broadband light and respectively transmit the first light ray and the second light ray to a second optical path and a third optical path, and the first light ray and the second light ray are parts of the broadband light;

a first fiber grating, connected to the first optical coupler through the second optical path and the third optical path, having a first reflection wavelength band, wherein the first fiber grating is configured to reflect a part of the first light ray whose wavelength band is within the first reflection wavelength band to generate a third light ray that returns to the first optical coupler along the second optical path and to reflect a part of the second light ray whose wavelength band is within the first reflection wavelength band to generate a fourth light ray that returns to the first optical coupler along the third optical path;

a second optical coupler configured to receive a fifth light ray from the first optical coupler through a fourth optical path, generate a sixth light ray in response to the fifth light ray, and transmit the sixth light ray to a fifth optical path, wherein the first optical coupler is configured to generate the fifth light ray in response to the third light ray and the fourth light ray, and the sixth light ray is a part or all of the fifth light ray;

a second fiber grating, connected to the second optical coupler through a fifth optical path, having a second reflection wavelength band, wherein the second fiber grating is configured to receive the sixth light ray from the second optical coupler through the fifth optical path and reflect a part of the sixth light ray whose wavelength band is within the second reflection wavelength band to generate a seventh light ray that returns to the second optical coupler along the fifth optical path; and a first photo receiver configured to receive an eighth light ray from the second optical coupler through a sixth optical path and generate a first electrical signal of a pulse waveform of vascular pulsation in response to the eighth light ray;

wherein the second reflection wavelength band shifts with a vascular pulsating stress of an object to be measured.

6. The blood pressure and heart rate measuring device according to claim 5, further comprising a second photo receiver configured to receive a ninth light ray from the second optical coupler through a seventh optical path and generate a second electrical signal in response to the ninth light ray, wherein the blood pressure and heart rate measuring device is configured to divide the first electrical signal by the second electrical signal to obtain a pulsating waveform signal, and the ninth light ray is a part or all of the fifth light ray.

7. The blood pressure and heart rate measuring device according to claim 5, wherein a deviation between 3 dB bandwidths of the first reflection wavelength band and the second reflection wavelength band is less than 2 nm and a deviation between central values of reflection wavelengths of the first reflection wavelength band and the second reflection wavelength band is less than 3 nm.

8. The blood pressure and heart rate measuring device according to claim 5, wherein a 3 dB wavelength bandwidth of the broadband light source ranges between 2 nm and 800 nm and a central wavelength of the broadband light source is within a wavelength range of visible light or infrared light.

9. A blood pressure and heart rate measuring device comprising at least:

a laser light source configured to provide laser light;

a first optical coupler connected to the laser light source through a first optical path and configured to receive the laser light, wherein the first optical coupler is configured to guide the laser light to a second optical path;

a first fiber grating, connected to the first optical coupler through the second optical path, having a first reflection wavelength band and a first transmission wavelength band, wherein the laser light from the first optical coupler passes through the first fiber grating;

an Er-doped fiber connected to the first fiber grating and configured to generate broadband light that returns to the first fiber grating in response to the laser light passing through the first fiber grating; wherein a part of the broadband light whose wavelength band is within the first transmission wavelength band passes through the first fiber grating to generate a first light ray that returns to the first optical coupler along the second optical path;

a second optical coupler configured to receive a second light ray from the first optical coupler through a third optical path, generate a third light ray in response to the second light ray, and transmit the third light ray to a fourth optical path, wherein the second light ray is a part or all of the first light ray and the third light ray is a part or all of the second light ray;

a second fiber grating, connected to the second optical coupler through the fourth optical path, having a second reflection wavelength band and a second transmission wavelength band, wherein the second fiber grating is configured to receive the third light ray from the second optical coupler through the fourth optical path and reflect a part of the third light ray whose wavelength band is within the second reflection wavelength band to generate a fourth light ray that returns to the second optical coupler along the fourth optical path; and a first photo receiver configured to receive a fifth light ray from the second optical coupler through a fifth optical path and generate a first electrical signal of a pulse waveform of vascular pulsation in response to the fifth light ray, wherein the fifth light ray is a part or all of the fourth light ray;

wherein the second reflection wavelength band shifts with a vascular pulsating stress of an object to be measured.

10. The blood pressure and heart rate measuring device according to claim 9, further comprising a second photo receiver configured to receive a broadband light ray from the Er-doped fiber through a sixth optical path or receive a sixth light ray from the second optical coupler through a seventh optical path to generate a second electrical signal, wherein the blood pressure and heart rate measuring device is configured to divide the first electrical signal by the second electrical signal to obtain a pulsating waveform signal, and the sixth light ray is a part or all of the second light ray.

11. The blood pressure and heart rate measuring device according to claim 9, wherein a deviation between 3 dB bandwidths of the first reflection wavelength band and the second reflection wavelength band is less than 2 nm and a deviation between central values of reflection wavelengths of the first reflection wavelength band and the second reflection wavelength band is less than 3 nm.

12. A blood pressure and heart rate measuring device comprising at least:

a broadband light source configured to provide broadband light;

a first fiber grating, connected to the broadband light source through a first optical path and configured to receive the broadband light, having a first reflection wavelength band and a first transmission wavelength band, wherein a part of the broadband light whose wavelength band is within the first transmission wavelength band passes through the first fiber grating to form a first light ray;

an optical coupler connected to the first fiber grating through a second optical path and configured to receive the first light ray;

a second fiber grating, connected to the optical coupler through a third optical path, having a second reflection wavelength band and a second transmission wavelength band, wherein the second fiber grating is configured to receive a second light ray from the optical coupler through the third optical path and reflect a part of the second light ray whose wavelength band is within the second reflection wavelength band to generate a third light ray that returns to the optical coupler along the third optical path, and the second light ray is a part or all of the first light ray; and a first photo receiver connected to the optical coupler through a fourth optical path and configured to receive a fourth light ray from the optical coupler through the fourth optical path and generate a first electrical signal of a pulse waveform of vascular pulsation in response to the fourth light ray, wherein the fourth light ray is a part or all of the third light ray;

wherein the second reflection wavelength band shifts with a vascular pulsating stress of an object to be measured.

13. The blood pressure and heart rate measuring device according to claim 12, further comprising a second photo receiver configured to receive a fifth light ray from the optical coupler through a fifth optical path and generate a second electrical signal in response to the fifth light ray, wherein the blood pressure and heart rate measuring device is configured to divide the first electrical signal by the second electrical signal to obtain a pulsating waveform signal, and the fifth light ray is a part or all of the first light ray.

14. The blood pressure and heart rate measuring device according to claim 12, wherein a deviation between 3 dB bandwidths of the first reflection wavelength band and the second reflection wavelength band is less than 2 nm and a deviation between central values of reflection wavelengths of the first reflection wavelength band and the second reflection wavelength band is less than 3 nm.

15. The blood pressure and heart rate measuring device according to claim 12, wherein a 3 dB wavelength bandwidth of the broadband light source ranges between 2 nm and 800 nm and a central wavelength of the broadband light source is within a wavelength range of visible light or infrared light.

16. A blood pressure and heart rate measuring device comprising at least:

a broadband light source configured to provide broadband light;

an optical coupler connected to the broadband light source through a first optical path and configured to receive the broadband light;

a first fiber grating, connected to the optical coupler through a second optical path, having a first reflection wavelength band and a first transmission wavelength band, wherein the first fiber grating is configured to receive a first light ray from the optical coupler through the second optical path and reflect a part of the first light ray whose wavelength band is within the first reflection wavelength band to generate a second light ray that returns to the optical coupler along the second optical path, with the first light ray being a part or all of the broadband light, and a part of the first light ray whose wavelength band is within the first transmission wavelength band passing through the first fiber grating to form a third light ray;

a second fiber grating, connected to the first fiber grating through a third optical path, having a second reflection wavelength band and a second transmission wavelength band, wherein the second fiber grating is configured to receive the third light ray from the first fiber grating through the third optical path and reflect a part of the third light ray whose wavelength band is within the second reflection wavelength band to generate a fourth light ray that returns to the optical coupler along the third optical path, the first fiber grating, and the second optical path; and a first photo receiver connected to the optical coupler through a fourth optical path and configured to receive a fifth light ray from the optical coupler through the fourth optical path and generate a first electrical signal of a pulse waveform of vascular pulsation in response to the fifth light ray, wherein the fifth light ray is parts or all of the second light ray and the fourth light ray;

wherein the first reflection wavelength band or the second reflection wavelength band shifts with a vascular pulsating stress of an object to be measured.

17. The blood pressure and heart rate measuring device according to claim 16, further comprising a second photo receiver configured to receive a sixth light ray from the optical coupler through a fifth optical path and generate a second electrical signal in response to the sixth light ray, wherein the blood pressure and heart rate measuring device is configured to divide the first electrical signal by the second electrical signal to obtain a pulsating waveform signal, and the sixth light ray is a part or all of the broadband light.

* * * * *